US007132104B1

(12) United States Patent
von Horsten et al.

(10) Patent No.: US 7,132,104 B1
(45) Date of Patent: Nov. 7, 2006

(54) MODULATION OF CENTRAL NERVOUS SYSTEM (CNS) DIPEPTIDYL PEPTIDASE IV (DPIV) -LIKE ACTIVITY FOR THE TREATMENT OF NEUROLOGICAL AND NEUROPSYCHOLOGICAL DISORDERS

(75) Inventors: Stephan von Horsten, Wedemark (DE); Ants Kask, Tallinn (EE); Hans-Ulrich Demuth, Halle (DE); Huu Phuc Nguyen, Hannover (DE); Susanne Kruber, Halle (DE); Matthias Hoffmann, Wengelsdorf (DE)

(73) Assignee: Probiodrug AG, Hàlle/Saale (DE)

( * ) Notice: Subject to any disclaimer, the term of this patent is extended or adjusted under 35 U.S.C. 154(b) by 25 days.

(21) Appl. No.: 10/014,291

(22) Filed: Oct. 26, 2001

Related U.S. Application Data

(60) Provisional application No. 60/244,036, filed on Oct. 27, 2000.

(51) Int. Cl.
*A61K 39/00* (2006.01)
*A61K 39/38* (2006.01)
*A61K 35/00* (2006.01)
*A01N 37/18* (2006.01)

(52) U.S. Cl. .............................. 424/198.1; 424/184.1; 424/185.1; 424/116; 514/19; 514/2

(58) Field of Classification Search .................... 514/2, 514/19; 424/94.1, 130.1; 435/183, 212, 435/195, 113
See application file for complete search history.

(56) References Cited

U.S. PATENT DOCUMENTS

| | | | |
|---|---|---|---|
| 2,961,377 A | 11/1960 | Shapiro et al. ............... | 167/65 |
| 3,174,901 A | 3/1965 | Sterne ......................... | 167/65 |
| 3,879,541 A | 4/1975 | Kabbe et al. ................. | 424/326 |
| 3,960,949 A | 6/1976 | Ahrens et al. .......... | 260/564 B |
| 4,024,250 A * | 5/1977 | Palm ........................... | 514/23 |
| 4,028,402 A | 6/1977 | Fischer et al. ......... | 260/501.14 |
| 4,935,493 A | 6/1990 | Bachovchin et al. ....... | 530/331 |
| 5,433,955 A | 7/1995 | Bredehorst et al. ........ | 424/94.3 |
| 5,462,928 A | 10/1995 | Bachovchin et al. ......... | 514/19 |
| 5,512,549 A | 4/1996 | Chen et al. ................... | 514/12 |
| 5,543,396 A | 8/1996 | Powers et al. ................ | 514/19 |
| 5,614,379 A | 3/1997 | MacKellar ................. | 435/68.1 |
| 5,624,894 A | 4/1997 | Bodor .......................... | 514/2 |
| 5,939,560 A | 8/1999 | Jenkins et al. .............. | 548/535 |
| 6,006,753 A | 12/1999 | Efendic ...................... | 128/898 |
| 6,319,893 B1 * | 11/2001 | Demuth et al. ................ | 514/2 |

FOREIGN PATENT DOCUMENTS

| | | |
|---|---|---|
| DE | 25 42598 A1 | 4/1976 |
| DE | 196 16 486 A1 | 10/1997 |
| DE | 299 09 210 U | 9/1999 |
| EP | 0 995 440 A1 | 4/2000 |
| FR | 2085665 | 3/1971 |
| FR | 2696740 | 4/1994 |
| JP | 04-288098 | 10/1992 |
| JP | 4334357 | 11/1992 |
| WO | WO 91/11457 | 8/1991 |
| WO | WO 91/16339 | 10/1991 |
| WO | WO 91/17767 | 11/1991 |
| WO | WO 93/08259 | 4/1993 |
| WO | WO 95/11689 | 5/1995 |
| WO | WO 95/15309 | 6/1995 |
| WO | WO 95/29691 | 11/1995 |
| WO | WO 97/40832 | 11/1997 |
| WO | WO 97/45117 | 12/1997 |
| WO | WO 98/19998 | 5/1998 |
| WO | WO 98/22494 | 5/1998 |
| WO | WO 99/46272 A | 9/1999 |
| WO | WO 00/01849 | 1/2000 |
| WO | WO00/01849 | 1/2000 |
| WO | WO 00/53171 | 9/2000 |
| WO | WO 01/62266 A2 | 8/2001 |

OTHER PUBLICATIONS

Lader, 1981, J.Clinical Psycopharmacology, vol. 1, No. 6, pp. 342-349.*
Tobin and Dusheck, , 1998, Asking about life, Sunders Coolege Publishing, p. 799.*
Campbell, I.W. New Antidiabetic Drugs, ed. C.J. Bailey & P.R. Flatt, Smith-Gordon, "Sulphonylureas and metformin: efficacy and inadequacy". 3:33-51 (1990).

(Continued)

*Primary Examiner*—Olga N. Chernyshev
(74) *Attorney, Agent, or Firm*—Sonnenschein Nath & Rosenthal LLP

(57) ABSTRACT

The present invention discloses a method for therapeutically treating an animal, including a human, for psychosomatic, depressive and neuropsychiatric diseases, such as anxiety, depression, insomnia, schizophrenia, epilepsy, spasm and chronic pain. Administration of a suitable DP IV inhibitor causes the reduction of activity in the enzyme dipeptidyl peptidase (DP IV or CD 26) or of DP IV-like enzyme activity in the brain of mammals and leads as a causal consequence to a reduced degradation of the neuropeptide Y (NPY) and similar substrates by DP IV and DP IV-like enzymes. Such treatment will result in a reduction or delay in the decrease of the concentration of functionally active neuronal NPY (1–36). As a consequence of the resulting enhanced stability of the endogenous NPY (1–36) caused by the inhibition of DP IV activity, NPY activity is prolonged thereby resulting among other things in functionally active NPY Y1 receptor activity thereby facilitating anti-depressive, anxiolytic, analgesic, anti-hypertension and other neurological effects.

3 Claims, 11 Drawing Sheets

OTHER PUBLICATIONS

Mercla Index, 11th Edition, p. 934, 1979.

Martindale The Extra Pharmacopeia, 30th Edition, Pharmaceutical Press, 1993, p. 1619.

Chemical Abstracts, vol. 115. No. 15, Oct. 14, 1991 Columbus, Ohio, US; abstract No. 149947q, Schoen Ekkehard et al: "Dipeptidyl peptidase IV in the immune system. Effects of specific enzyme inhibitors on activity of dipeptidyl peptidase IV and proliferation of human lymphocytes".

Chemical Abstracts, vol. 126, No. 2, Jan. 13, 1997 Columbus, Ohio, US; abstract No. 16161j, Stoeckel A. et al: "Competitive inhibition of proline specific enzymes by amino acid thioxopyrrolidides and thiazolidides".

Chemical Abstracts, vol. 118, No. 25, Jun. 21, 1993 Columbus, Ohio, US; abstract No. 255342k, Hosoda, et al, "Preparation of N-(heterocyclic Carbonyl) Amino Acids and Analogs as Prolyl Endopeptidase Inhibitors", Nov. 20, 1992.

Arai et al: "Synthesis of prolyl endopeptidase inhibitors and evaluation of their structure-activity relationships : in vitro inhibition of prolyl endopeptidase from Canine Brain" Chemical and Pharmaceutical Bulletin., Bd. 41, Nr. 9, 1993.

J. Lin et al.: "Inhibition of depeptidyl peptidase IV by fluoroolefin-containing n-peptidyl-O-hydroxylamine peptidomimetics" Proceedings of the National Academy of Sciences of USA, vol. 95, Nov. 1998, pp. 14020-14024.

Korom, S., et al "Inhibition of CD26/dipeptidyl peptidase IV activity in vivo prolongs cardiac allograft survival in rat recipients", Transplantation vol. 63, 1495-1500 No. 10 (1997).

Tanka, S., et al., "Suppression of arthritis by the inhibitors of dipeptidyl peptidase IV". Int. J. Immunopharmacol, vol. 19, No. 1 pp. 15-24, 1997.

Mentlein, R., et al., "Proteolytic processing of neuropeptide Y and peptide YY by dipeptidyl peptidase IV". Regul. Pept. 49, 133-144(1993).

Wetzl, W., et al., "Effects of the CLIP fragment ACTH 20-24 on the duration of REM sleep episodes". Neuropeptides, 31, 41-45 (1997).

Amasheh, S., et al., "Electrophysiological analysis of the function of the mammalian renal peptide transporter expressed in *Xenopus laevis* oocytes". J. Physiol. 504, 169-174 (1997).

Durinx, C.; et al.; "Reference Values for Plasma Dipeptidyl-Pepidase IV activity and their Association with Other Laboratory Parameters". Clin Chem Lab Med 2001, Feb.; 39 (2) :155-9, 1 page.

Gossrau, R.; "Cytochemistry of Membrane Proteases". Histochem J, Jul. 1985; 17 (7) :737-71, 1 page.

Hahn, T.; et al.; "Enzyme Histochemical Evidence for the Presence of Potential Blood Pressure Regulating Proteases in Cultured Villous Explants from Human First Trimester Placentae". Acta Histochem 1993, Dec., 1995 (2) :185-92, 1 page.

Heymann, E.; et al.; "Has Dipeptidyl Peptidase IV an Effect on Blood Pressure and Coagulation." Klin Wochenschr, Jan., 1984, 2;62 (1) :2-10, 1 page.

Magyar, C.E.; et al.; "Proximal Tubule Na Transporter Responses are the same during Acute and Chronic Hypertension." Am J Physiol Renal Physiol, Aug. 2000; 279 (2) :F358-69, 1 page.

Papies, B.; et al.; "Isoenzyme (Lactate Dehydrogenase, Aspartate Aminotransferase) and Dipeptidyl Peptidase IV Activity Changes in Blood Plasma Likely Indicative of Organ Involvement due to Arterial Hypertension." Cor Vasa, 1991; 33 (3) :218-26, 1 page.

Qureshi. N.U.; et al., "Endogenous Neuropeptide Y Mediates Vasoconstriction during Endotoxic and Hemorrhagic Shock". Regul Pept, Sep. 25, 1998; 75-76:215-20, 1 page.

Index Nominum, International Drug Directory 1992/1993, Medpharm Scientific Publishers, pp. 728-729.

The Merck Index, 9th Edition, 1976, p. 773.

C.J. Bailey et al., *New Antidiabetic Drugs*, Smith-Gordon Nishimura, 1990, p. 36.

The Merck Index, 12th Edition, An Encyclopedia of Chemicals, Drugs, and Biologicals, 1996, p. 1014.

Martindale The Extra Pharmacopoeia, 30th Edition, London Pharmaceutical Press, 1993, p. 36.

Heymann, E.; et al.; "Has Dipeptidyl Peptidase IV an Effect on Blood Pressure and Coagulation." Klin Wochenschr, Jan., 1984, 2;62 (1) :2-10, 1 page.

The Merck Index, An Encyclopedia of Chemicals and Drugs, 9th Edition, Merck & Co., Inc., 1976, p. 773.

C.B. Welch, *Medical Management of Non-Insulin-Dependent (Type II) Diabetes*, 3rd edition, American Diabetes Association, "Diagnosis and Classification" p. 3, 1994, Pharmacologic Intervention (2 pages).

Mannucci et al., *Diabetes Care*, "Effect of Metformin on Glucagon-Like Peptide 1 (GLP-1) and Leptin Levels in Obese Nondiabetic Subjects", 24(3): 489-494, Mar. 2001.

Stryer, *Biochemistry 3rd Ed.*, "Protein Conformation, Dynamics, and Function", 1988, p. 191-193.

Pauly et al., *Regulatory Peptides*, "Abstracts Issue: Abstracts from the 11th International Symposium on Regulatory Peptides", Jul. 15, 1996, 64(1-3): 148 plus cover.

Gutniak et al., *New England Journal of Medicine*, "Antidiabetogenic Effect of Glucagon-like peptide-1 (7-36) Amide in Normal Subjects and Patients With Diabetes Mellitus", 1992, 326: 1316-1322.

H.A. Smith et al., *Veterinary Pathology* (fourth edition), "Diseases and Disorders of Metabolism: Deficiency Diseases", 1972, p. 1018-1020.

G.G. Duncan, *Diseases of Metabolism (Asian edition)*, "Diabetes Mellitus", p. 951-957.

T.J. Kieffer et al., "Degradation of Glucose-Dependent Insulinotropic Polypeptide and Truncated Glucagon-Like Peptide 1 In Vitro and In Vivo by DP IV", Endocrinology, vol. 136(8), 1995, p. 3585-3596.

C.F. Deacon et al., *Diabetes*, "Both Subcutaneously and Intravenously Administered Glucagon-Like Peptide I Are Rapidly Degraded from the $NH_2$-Terminus in Type II Diabetic Patients and in Healthy Subjects", Sep. 1995, 44: 1126-1131.

*Vidal*, 1993, 69th Edition, p. 612-613.

*Goodman & Gilman's The Pharmacological Basis of Therapeutics*, Ninth Edition, 1996,p. 1510.

Nathan et al., *Diabetes Care*, "Insulinotropic Action of Glucagon-like Peptide-1-(7-37) in Diabetic and Nondiabetic Subjects", Feb. 1992, 15(2):270-275.

*Pschyrembel*, Kininisches Wörterbuch 257, Auflage, 1994, 9 pages.

Frohman et al., *Journal of Clin. Invest.*, "Rapid Enzymatic Degradation of Growth Hormone-releasing Hormone by Plasma in Vitro and in Vivo to a Biologically Inactive Product Cleaved at the $NH_2$ Terminus", vol. 78, Oct. 1986, p. 906-913.

Snow et al., *Advances In Medicinal Chemistry*, "Boronic Acid Inhibitors of Dipeptidyl Peptidase IV: A New Class of Immunosuppressive Agents", vol. 3, 1995, p. 149-177.

Ashworth et al., *Bioorg. Med. Chem. Lett.*, "2-Cyanopyrrolidides as Potent, Stable Inhibitors of Dipeptidyl Peptidase IV", 1996, 6(10): 1163-1166.

Endroczi et al., *Acta Physiol. Hung.*, "Dipeptidyl peptidase IV (DP IV) and Superoxide Dismutase Activity in Thymus-Derived Lymphocytes: Effects of Inhibitory Pepdides and $ZN^{2+}$ in Vitro", 1990, 75(1): 35-44.

Lee, H.S. et al., "Cathepsin B Inhibitory Peptides Derived from β-Casein," Peptides 21 (2000) 807-809.

Edwards, J.V. et al., *J. Peptide Res.*, "Synthesis and Activity of $NH_2$ -and COOH-Terminal Elastase Recognition Sequences on Cotton," 1999, 54: 536-543.

* Wettstein, J.G. et al. *Pharmacology & Therapeutics*, "Central Nervous System Pharmacology of Neuropeptide Y.", 1995, 65(3): 397-414.

* Badia-Elder N.E. et al., *Alcoholism Clinical and Experimental Research*, "Effects of Neuropeptide Y (NPY) on Ethanol Intake and Anxiety in High and Low Alcohol Drinking (HAD1/LAD1) Rats.", 2000, 24(5): 82A.

* Munglani R. et al., *Drugs, Adis International Ltd, At*, "The Therapeutic Potential of Neuropeptide Y Analgesic, Anxiolytic and Antihypertensive", 1996 52(3): 371-389.

* cited by examiner

MODULATION OF CENTRAL NERVOUS SYSTEM (CNS) DIPEPTIDYL PEPTIDASE IV (DPIV) -LIKE ACTIVITY FOR THE TREATMENT OF NEUROLOGICAL AND NEUROPSYCHOLOGICAL DISORDERS

RELATED APPLICATION

This application claims the benefit of Provisional Application No. 60/244,036 filed on Oct. 27, 2000 which is incorporated herein by reference.

BACKGROUND OF THE INVENTION

1. Field of the Invention

The present invention relates to the function of DPIV-like enzymes within the CNS and their biological effects on neuropeptide levels, neurotransmission and behavior. The present invention also relates to the potentiation of endogenous neurological and neuropsychological effects of brain neuropeptide Y (NPY) systems and other substrates of DPIV by selective inhibition of DPIV-like enzymes. The invention relates further to the treatment of hypertension, fever, sleep dysregulation, anorexia, anxiety related disorders including depression, seizures including epilepsy, drug withdrawal and alcoholism, neurodegenerative disorders including cognitive dysfunction and dementia, and neuropsychiatric disorders including schizophrenia, via a potentiation of NPY Y1 receptor mediated effects resulting from an inhibition of DPIV-like activity within the CNS.

2. Background Art

CNS neuropeptide systems, peptide degradation and stress related diseases daptive responses initiate sequential steps of transmitter release in the CNS with corticotropin releasing hormone (CRH) being a key integrator (Dunn and Berridge, 1990; Koob and Heinrichs, 1999). Other neurotransmitters may modulate the course and outcome of CRH-induced behavioral, endocrine and immunological alterations. It has been demonstrated that endogenous neuropeptide Y (NPY) exert anti-CRH-like effects (Heilig et al., 1994; Thorsell et al., 1999; Britton et al., 2000). Recent clinical data implicate CRH in the etiology and pathophysiology of a variety of endocrine, psychiatric, neurodegenerative, and immunological disorders (Behan et al., 1995; Dieterich et al., 1997; Linthorst et al., 1997; Owens and Nemeroff, 1991; Wilder, 1993). Apart from selective receptor blockade of CRH receptors, an increase of endogenous anti-CRH-like acting NPY may therefore be beneficial. The relative increase of an endogenous NPY-like tone may be pharmacologically achieved by either increased degradation of CRH or by inhibition of the degradation of NPY. NPY is a substrate for the enzyme DPIV. A modulation of CNS DPIV-like activity provides, therefore, a new treatment regime of neurological and neuropsychological disorders.

DPIV and NPY

DPIV (CD26; EC 3.4.14.5) is an ectopeptidase with a triple functional role. DPIV is involved in truncation of Xaa-Pro dipeptides, circulating hormones and chemokines (Mentlein et al., 1999; Pauly et al., 1999), in T cell dependent immune responses (Kahne et al., 1999; Korom et al., 1997) and in metastasis (Cheng et al., 1998; 2000). DPIV selectively cleaves peptides after penultimate N-terminal proline and alanine residues. Endogenous substrates for this enzyme include the incretins, such as glucose-dependent insulinotropic polypeptides, like GIP and GLP-1. In the presence of DP IV, these hormones are enzymatically degraded to inactive forms. NPY is one of the best, if not the best, substrates of DPIV-like enzymically activity (Mentlein, 1999). So far, the function of DPIV-like enzymatic activity within the CNS is not understood nor is the modulation of CNS DPIV-like activity the objective of any pharmacological treatment regime.

Neuropeptide Y, peptide YY and pancreatic polypeptide share an evolutionary conserved proline-rich N-terminal sequence, a structure generally known to be inert to the attack of common proteinases, but a potential target for specialized proline-specific aminopeptidases. Mentlein et al. examined purified human DPIV, that liberated N-terminal Tyr-Pro from both, neuropeptide Y and peptide YY, with very high specific activities and $K_m$ values in the micromolecular range, but almost no Ala-Pro from pancreatic polypeptide. Other proline-specific aminopeptidases exhibitet low (aminopeptidase P) or totally no activity (dipeptidyl peptidase II). When human serum was incubated with neuropeptide Y or peptide YY at micro- and nanomolar concentrations, Tyr-Pro was detected as a metabolite of both species. Formation of Tyr-Pro in serum was blocked in the presence of Lys-pyrrolidine and diprotin A (Ile-Pro-Ile), specific competetive inhibitors of dipeptidyl peptidase IV. Incubation of neuropeptide Y or peptide YY with immunocytochemically defined, cultivated endothelial cells from human umbilial cord also yielded Tyr-Pro. Dipeptidyl peptidase IV could be immunostained on most endothelial cells by a specific antibody. They suggest, that dipeptidyl peptidase IV might be involved in the degradation of neuropeptide Y and peptide YY to N-terminal truncated neuropeptide Y (3–36) and peptide YY (3–36). Since specific binding to Y1, but not to Y2 subtype of neuropeptide Y/peptide YY receptors requires intact N— as well as C-termini of neuropeptide Y and peptide YY, removal of their amino-terminal dipeptides by dipeptidyl peptidase IV inactivates them for binding to one receptor subtype (Mentlein et al. 1993).

Discovery of NPY

Neuropeptide Y (NPY), a 36 amino acid peptide belonging to the pancreatic polypeptide family, was first isolated from porcine brain in 1982 (Tatemoto and Mutt, 1982). NPY is present in all sympathetic nerves innervating the cardiovascular system and is the most abundant peptide in the brain and the heart. Additionally, in rats, but not in humans, NPY is also found extraneuronally in platelets and endothelium (Zukovska-Grojec et al., 1993). Originally, NPY was known as a potent vasoconstrictor and a neuromodulator. Released by stress, exercise, and myocardial ischemia, NPY has been implicated in coronary heart disease, congestive heart failure, and hypertension (Zukovska-Grojec et al, 1998). More recently, because of the potent ability of NPY to stimulate food intake, it is suspected to play a role in obesity and diabetes (Kalra et al., 1999). Latest findings indicate, that NPY is also a mitogen for rat aortic vascular smooth muscle cells (Zukovska-Grojec et al., 1999).

NPY-related research has focussed on at least three main directions: (1) Co-transmission and sympathetic vasoconstriction, because of its co-expression with noradrenaline; (2) neurotransmission and function within the CNS, because of potent consummatory effects; and (3) evolution of NPY, since NPY is one of the most highly conserved bio-active peptides known (Colmers and Wahlestedt, 1993; Lundberg, 1996; Wahlestedt and Reis, 1993; Wettstein et al., 1996). NPY acts on at least six receptors (Y1–Y6), with varying peptide pharmacology and distinct distribution in the CNS (Gehlert, 1998) (Tab. 1).

Distribution of NPY, NPY Receptor Subtypes and mRNA

The distribution of NPY itself, NPY receptor protein and their mRNA within the CNS of human and rat brains has recently been reviewed (Dumont Y, Jacques D, St-Pierre, J.-A., Tong, Y., Parker, R., Herzog H. and Qurion, R., 2000; in Handbook of Chemical Neuroanatomy, Vol. 16: Peptide Receptors, Part I; Quirion, R., Björklund, A. and Hökfeld, T., editors). A brief survey is given in Tab. 1.

NPY-containing neurons are evident in the nasal mucosa of various species including man, often associated with glandular acini and blood vessels (Baraniuk et. Al., 1990; Grunditz et. al., 1994). Stimulation of the parasympathetic nerve supply to the nasal mucosa (vidian nerve) in dogs increases blood flow in the region and causes mainly atropine resistance. Intravenous administration of NPY reduces vasodilitation due to parasympathetic nerve stimulation, an effect that was not mimicked by the NPY Y1-selective agonist [Leu31, Pro34]NPY, but was mimicked by administration of the NPY Y2-receptor agonist N-acetyl[Leu28, Leu31JNPY(24–36) (Lacroix et al., 1994). This is consistent with a prejunctional NPY Y2-like receptor-mediated inhibition of transmitter release from parasympathetic nerve terminals.

NPY Receptor Function

Since the discovery of NPY in 1982, it became apparent that NPY is involved in the regulation of several behavioral and physiological functions (Colmers and Wahlestedt, 1993; Wettstein et al., 1996) (Tab. 1). In the brain, NPY has been implicated in anxiety and depression, feeding and obesity, memory retention, neuronal excitability, endocrine function, and metabolism (Gehlert, 1998). NPY is unarguably the most abundant neuropeptide discovered to date, with a wide distribution in the CNS and the peripheral nervous system (PNS). NPY forms a family of peptides together with peptide YY (PYY) (approximately 70% homology) and pancreatic polypeptide (PP) (approximately 50% homology); both NPY and PYY are extremely bio-active, whereas PP is generally much less active (Gehlert, 1998; Wahlestedt and Reis, 1993) (Tab. 2).

Receptors for neuropeptide Y are also located on sensory nerve terminals and their activation can modulate local neurogenic responses (Grundemar et al., 1990; 1993). Two receptor subtypes have been called neuropeptide Y Y1 (postjunctional) and neuropeptide Y Y2 (prejunctional) on the basis of the different responses to a truncated analog of the related peptide YY-(13–36), when compared with neuropeptide Y in in vitro assay systems (Wahlestedt et al., 1986). Activation of neuronal prejunctional NPY receptors generally inhibits nerve activity, reducing the release of neurotransmitters in response to nerve impulses and in response to local factors acting to release neurotransmitters (Wahlestedt et al., 1986). The prejunctional or neuropeptide Y Y2 receptor classification was based on actions of peptide YY (13–36) but in many systems this molecule, as well as neuropeptide Y-(13–36), does exhibit pressor activity (Rioux et al., 1986; Lundberg, et al., 1988; Potter et al., 1989). This has been interpreted by some to indicate that in some vascular beds there are two types of neuropeptide Y receptors (both neuropeptide Y Yj and neuropeptide Y2) on postjunctional membranes (Schwartz et al., 1989). However the lack of selectivity of these molecules may be due to retention of partial agonistic activity on Yj receptors, which permits them to evoke a reduced functional response. Previously, a 13–36 analog of neuropeptide Y, (Leu 17, Glu", Ala 21, Ala 22, Glu 23, LeU28, LeU31) neuropeptide Y-(13–36) (ANA neuropeptide Y-(13–36)) which displayed prejunctional activity equivalent to the whole neuropeptide Y molecule in studies in vivo was described (Potter et al., 1989).

Apart from these historically well-defined neuropeptide Y receptors the existence of a number of other subtypes (Y3, Y4, Y5 and Y6) has been suggested on a pharmacological basis (Michel et al., 1998) and details of the cloning of receptors corresponding to Y1, Y2, Y4 and Y5 have been published (Herzog et al., 1992; Gerald et al., 1995; Bard et al., 1995; Gerald et al., 1996) (Tab. 1). The distribution and physiological significance of these various receptor subtypes has yet to be defined. Although some controversy has existed about the selectivity of truncated forms of neuropeptide Y for one or other receptor subtype (Potter et al., 1989), the emerging picture supports the initial classification into pre- and postjunctional receptor subtypes. Cell lines have been developed which express specifically one neuropeptide Y receptor subtype and the development of receptor-selective analogs of neuropeptide Y has focussed mainly on binding characteristics in these cell lines (Sheikh et al., 1989; Aakerlund et al., 1990; Fuhlendorff et al., 1990). More recently, a cDNA encoding the neuropeptide Y Y1 receptor has been cloned and cell lines expressing the cloned receptor have been analyzed for both specific binding of neuropeptide Y analogs (Herzog et al., 1992) and functional responses elicited by specific analogs. From such binding studies, combined with subsequent studies in vivo, two analogs have been classified as acting specifically on the postjunctional neuropeptide Y Y1 receptor. These neuropeptide Y Y receptor selective analogs, (Pro 34) neuropeptide Y and (Leu", Pro 34) neuropeptide Y, mimic the action of neuropeptide Y in raising blood pressure, and also share similar binding to cell lines expressing only neuropeptide Y Y receptors e.g. the human neuroblastoma cell line SK-N-MC and fibroblast lines expressing the cloned neuropeptide Y Y, receptor (Herzog et al., 1992). Neither exhibits the neuropeptide Y Y2 receptor action an inhibition of cardiac vagal action in vivo, a manifestation of inhibition of acetylcholine release (Potter et al., 1991; Potter and McCloskey, 1992).

TABLE 1

DISTRIBUTION AND FUNCTION OF NPY RECEPTOR SUBTYPES WITHIN THE CNS

| Receptor-subtype | CNS Expression | Function | Selective Agonist | Selective Antagonist or selectivity |
|---|---|---|---|---|
| Y1 | Cortex, etc. | Anxiolysis, LHRH Release | Intact N - Terminus: [Leu31, Pro34]NPY | BIBP3226; BIBO 3304 |
| Y2 | Hippocampus, Hypothalamus | Antiamnestic | C-terminale End: PYY3–36; PYY13–36 | T4[NPY(33–36)]4; BIIE0246 |
| Y3 | Ncl. Tractus Solitarius (NTS) | Bradycardia, Hypotension | NPY >> PYY, [Leu31, Pro34]NPY | PYY - Insensitivity |

TABLE 1-continued

DISTRIBUTION AND FUNCTION OF NPY RECEPTOR SUBTYPES WITHIN THE CNS

| Receptor-subtype | CNS Expression | Function | Selective Agonist | Selective Antagonist or selectivity |
|---|---|---|---|---|
| Y4 | Dorsal vagal Complex (DVC) | Emetic | PP >> NPY, PYY | PP - Preferring |
| Y5 (a) | Hypothalamus | Feeding | NPY, PYY, [Leu31, Pro34]NPY | [Leu31, Pro34]NPY-sensitive, BIBP3226 - non-reversible |
| Y5 (b) or Y6 | Hypothalamus | ?; species specific | ? | ? |

Tab. 1: NPY Receptor subtypes within the CNS;
? = unknown or not investigated

The development of the high affinity, non-peptide NPY antagonists, BIBP3226 and BIBO3304, has facilitated the functional characterization of NPY receptors, as this compound shows selectivity for Y1R, being devoid of activity on at least Y2R, Y3R and Y4R (Doods et al., 1996). Recently, a two Y2 receptor antagonist has been described. One is a TASP-molecule (Grouzmann et al., 1997), the other a non-peptide antagonist (Wieland et al., 1999) and other non-peptide receptor specific compounds became available (Daniels et al., 1995). Thus, specific receptor blockade within the brain would allow the functional characterization of behavioral and physiological effects mediated by central NPY receptors. In addition, mice lacking the Y1R were generated and are available (Pedrazzini et al., 1998). Neurons showing NPY-like immunoreactivity and NPY receptor expression are abundant in the CNS (Tab. 1), and perhaps are most notably found in hypothalamic and so-called limbic structures, but are also co-localized with brain stem monoaminergic neurons and cortical GABA-ergic neurons (Chronwall, 1985; Dumont et al., 1996). The latter may be of particular importance, because the GABA-benzodiazepine receptor complex is an important negative modulator of CRH secretion and of responsiveness to excitatory stimuli in rats and humans (Gear et al., 1997; Smith et al., 1992; Judd et al., 1995).

TABLE 2

RECEPTOR SUBTYPES UND PEPTIDE SELECTIVITY

| Receptor subtype | Peptide Potency |
|---|---|
| Y1-like | |
| Y1 | NPY = PYY = Pro$^{34}$-NPY > PP > NPY$_{13-36}$ |
| Y4 | PP >> NPY = PYY = LP-NPY > NPY$_{13-36}$ |
| Y6 | NPY = PYY = Pro$^{34}$-NPY > NPY$_{13-36}$ > PP |
| Y2-like | |
| Y2 | NPY = PYY = NPY$_{13-36}$ > Pro$^{34}$-NPY > PP |
| Y5-like | |
| Y5 | NPY = PYY = Pro$^{34}$-NPY > NPY$_{13-36}$ > PP |
| Not cloned | |
| PP receptor | PP >> PYY = NPY |
| Y3 | NPY = Pro$^{34}$-NPY = NPY$_{13-36}$ >> PYY |
| PYY-preferring | PYY > NPY >> NPY$_{13-36}$ >> Pro$^{34}$-NPY |

Tab. 2: Receptor subtypes and peptide selectivity according to Gehlert, 1998.

As has to be demonstrated, most of the central NPY effects are opposite to those observed after CRH application, stress or those which are found in anxiety related disorders. NPY almost completely resemble the effects produced by benzodiazepine application.

NPY and Autonomic Regulation

With respect to autonomic regulation, the results of Egawa et al. and others on i.c.v. CRH- and i.c.v. NPY-(Egawa et al., 1990; 1991; van Djik et al., 1994) mediated effects on sympathetic firing rate to brown adipose tissue (IBAT) demonstrate that CRH increases while NPY reduces the sympathetic outflow. These effects support the anti-stress-like functional role of CNS NPY systems.

NPY and Immune Functions

The immune system is also affected by NPY. Here, similarly to CRH-mediated effects, the effects of NPY could be subdivided into direct and indirect (centrally) mediated effects (von Hörsten et al., 1998a). I.c.v. applied NPY, and derived peptides, affect innate immune function, IL-6 levels, and leukocyte subsets, and these effects display dose, time, receptor, and compartment specificity (von Hörsten et al., 1998a, b, c). Since NPY immunoreactivity increases in the brain after peripheral induction of acute monoarthritis (Bileviciute et al., 1995), increased brain NPY levels may reflect partly an adaptive response to changes induced by inflammation. Importantly, the long lasting immunostimulatory action of i.c.v. NPY parallels the effects of Methionine-Enkephalin (MET-ENK) (von Hörsten et al., 1998c). Thus, while central CRH appears to be a key mediator of stress effects on the innate immune system (Irwin, 1994), NPY may interact with CRH or even antagonize its effects. The benzodiazepine-like action of NPY in conjunction with data demonstrating that benzodiazepines abrogate CRH-induced suppression of NK cell function (Irwin et al., 1993), further support the hypothesis, suggesting an anti-CRH-like, "stress-protective" action of NPY receptors activation.

NPY and Central Cardiovascular Regulation

The highest levels of NPY Y1, Y2, Y4 and Y5 receptors are found in the nucleus tractus solitarius (NTS), the area postrema and the dorsal vagal complex in the rat brain. These receptors are likely to be involved in the CNS-mediated effects of NPY on various cardiovascular and respiratory parameters (Dumont et al, 1992; McAuley et al., 1993). For example, direct injections of NPY into the NTS produce vasodepressor effects and suppressed baroreceptor reflexes (Grundemar et al, 1992; Shih et al., 1992). These effects may be mediated via the Y2 or the Y3 receptor based on the relative potency of NPY$_{13-36}$ (Narvaez et al, 1993) but no potency of PYY (Grundemar et al., 1991a, b). Thus, within the CNS, brainstem NPY systems may exert anti-hypertensive effects. These central effects of NPY appear to be opposite to the periphery. In the peripheral cardiovascular system, NPY raises blood pressure by an action on post-junctional Y receptors and inhibits neurotransmitter release—both acetylcholine and noradrenaline—by acting on prejunctional neuropeptide Y receptors. When administered intravenously, NPY produces a potent and long-lasting vasoconstriction that is not blocked by alpha or beta adrenergic antagonists (Wahlestedt et al., 1986).

NPY and Thermoregulation

Potent hypothermic effects of NPY have been described (Esteban et al., 1989; Jolicoeur et al., 1991; Currie and Coscina, 1995). Interestingly, Y1 receptor antisense-treated rats demonstrated increases in body temperature (Lopenz-Valpuesta et al, 1996), suggesting that the Y1 receptor subtype could be responsible for the hypothermia induced by NPY. No further studies or pharmacological approaches explored the possibility that NPY Y1 receptor activation might be useful in the treatment of fever.

NPY, Circadian Rhythms and Sleep

The suprachiasmatic nucleus in conjunction with the geniculo hypothalamic tract is of critical importance in diurnal rhythms (Albers and Ferris, 1984; Meijer and Reitveld, 1989). The effect of NPY on circadian rhythms is believed to be mediated in the suprachiasmatic nucleus (Biello et a., 1994; Human and Albers, 1994) and the Y2 receptor subtype has been implicated in the effect (Golombeck et al., 1996; Human et al., 1996) by modulating glutamatergic neuronal activity (Biello et al., 1997). However, considering the effect of NPY on GABAergic neurons in the suprachiasmatic nucleus (Chen and van den Pol, 1996; Biggs and Prosser, 1999), it appears that other NPY receptor subtypes could also play a role in modulation of circadian rhythms.

Disturbance of sleep is a common health problem and often associated with depression. In rats i.c.v. NPY treatment has been demonstrated to overcome CRH-induced and stress-induced shortening of sleep (Yamada et al., 1996). With regard to sleep regulation in humans, Ehlers et al., (1997) found that "dysregulation" of sleep and arousal states in depression and anxiety may be consistent with an upset of the balance between hypothalamic neuropeptide systems for NPY and CRH. Antonijevic et al. (2000) reported that NPY promotes sleep and inhibits the hypothalamo-pituitary-adrenocortical (HPA) axis in humans, pointing to a possible role of NPY agonists for the development of novel treatment strategies for affective disorders. Since in major depression increased HPA-activity, sleeping disorder, anxiety and loss of appetite are main characteristics these findings further support a role of NPY in anxiety-disorders. Thus, a pharmacologically induced increased of NPY levels might exert sleep-promoting effects. Yet, pharmacological approaches to increase NPY levels are needed.

NPY and Nociception

Interestingly, NPY has also been reported to modulate nociception. There is evidence, that centrally (i.c.v.) applied NPY induces hyperalgesic effects on hot plate latency in mice (Mellado et al., 1996) and rats (von Hörsten et al., 1998c). These results also parallel the finding that benzodiazepines antagonize opioid and opiate analgesia via enhanced action of GABA at the GABA-A receptors (Gear et al., 1997). At a spinal level, in the dorsal root ganglia, NPY appears to exert analgesic-like effects and an increase of NPY Y2 receptor mRNA as well as NPY-like immunoreactivity has been reported after sciatic nerve lesions (Zhang et al., 1993). However, the physiological role of NPY in nociception remains to be established.

NPY and Feeding

On a behavioral level, most of the research has focussed on the potent orexigenic effects of NPY (Clark et al, 1984; Marsh et al., 1998; Kalra et al., 1999; O'Shea, et al., 1997; Stanley and Leibowitz, 1985). The orexigenic effect of NPY parallels the known orexigenic "side" effect of benzodiazepine treatment, and is opposite to the anorexigenic effect of CRH. CRH and NPY antagonize their feeding effects (Heinrichs et al., 1993; Menzaghi et al., 1993). I.c.v. CRH stopped weight gain in genetically obese (fa/fa) NPY overexpressing rats (Bchini-Hooft et al., 1993), and it was shown that the hypothalamic NPY feeding system is largely dependent on circulating corticosterone (Stanley et al., 1989). Chronic i.c.v. infusion of NPY has been demonstrated to decrease hypothalamic content of CRH (Sainsbury et al., 1997). Possibly, the induction of hunger by increased hypothalamic NPY content affects other motivational systems. Structure-affinity and structure-activity relationship studies of peptide analogs, combined with studies based on site-directed mutagenesis and anti-receptor antibodies, have given insight into the individual characterization of each receptor subtype relative to its interaction with the ligand, as well as to its biological function. A number of selective antagonists at the Y1-receptor are available whose structures resemble that of the C-terminus of NPY. With respect to the behavioral regulation of feeding behavior, some of these compounds, like BIBP3226, BIBO3304 and GW 1229, have recently been used for in vivo investigations of the NPY-induced increase of food intake (Cabrele and Beck-Sickinger, 2000) and is was found that probably Y1 and Y5 receptors are involved in the mediation of these effects (Wieland et al., 1998).

NPY, Anxiety and Depression

Anxiolytic-like effects of NPY have been demonstrated using the elevated plus maze test (Montgomery), the punished drinking test (Vogel), and the punished responding test (Geller-Seifter), with potency and efficacy matching those of benzodiazepines (Griebel, 1999; Heilig et al., 1989; Wettstein et al., 1995). NPY acts anxiolytic-like on the response to novelty (Heilig and Murison, 1987; von Hörsten et al., 1998b), and produces anxiolytic-like effects on the elevated plus maze and other anxiety related tests (Wahlstedt and Reis, 1993; Wahlestedt et al., 1993). Interestingly, Y1 receptor antisense-treated rats showed marked anxiety-related behaviors, without alterations of locomotor activity and food intake (Wahlestedt et al., 1993). Additionally, in the Flinder rat strain, a genetic model of depression, Y1 receptor mRNA expression was decreased in different cortical regions and the dentate gyrus of the hippocampus, while Y2 receptor mRNA expression did not differ from controls (Caberlotto et al., 1998). Olfactory bulbectomy in the rat has been developed as a model of depression (Leonard and Tuite, 1981). In this model, most of the changes resemble those found in depressed patients (Song et al., 1996). A 7-day i.c.v. administration of NPY in olfactory bulbectomized rats attenuated behavioral and neurotransmitters deficits in this model (Song et al., 1996). All these data argue for a role of NPY in anxiety-related disorders. NPY Y1, Y2, and possibly Y5 receptors, seem to be involved in the regulation of anxiety levels in rodents, with Y1-mediated effects being best characterized (Heilig et al., 1993; Kask et al., 1998b). Again, in comparison with benzodiazepines, anxiolysis is one of the most important properties of these compounds, especially of those affecting central CRH systems (e.g. Alprazolam) (Arvat et al., 1998; Korbonits et al., 1995; Kravitz et al., 1993; Torpy et al., 1993). It can be concluded, therefore, that endogenous NPY counteracts stress and anxiety (Heilig et al., 1994). Furthermore, these data suggest that the Y1 receptor subtype could be implicated in anxiety- and depression-related behaviors. Additionally, Kask et al. (1996)

reported that i.c.v. injection of the Y1 antagonist, BIBP3226, produced anxiogenic-like effects in the elevated plus-maze test, without any locomotor deficit. This effect can be reproduced by the administration of BIBP3226 in the dorsal periaqueductal gray matter but not in the locus coeruleus o the paraventricular nucleus of the hypothalamus (Kask et al., 1998c). Moreover, BIBP3226 and GR231118 administered into the dorsal periaqueductal gray matter decreased the time spent in active social interaction in rats (Kask et al., 1998d). These data suggest that endogenous NPY, under stressful and non-stressful conditions, relieve anxiety via the Y1 receptor.

The brain regions which are important for the anti-stress action of NPY include but may not be limited to the amygdala (Sajdyk et al., 1999, Thorsell et al., 1999), locus coeruleus (Kask et al., 1998c) and dorsal periaqueductal gray (Kask et al., 1998a, b). Amygdala NPY is not released under low stress conditions since blockade of NPY $Y_1R$ with BIBP3226 or BIBO3304 did not increase anxiety as measured in the elevated plus-maze and social interaction tests (Kask et al., 1998b; Sajdyk, 1999). Constant NPY-ergic tone, however, seems to exist in the dorsal periaqueductal gray matter, where the NPY $Y_1R$ antagonist had anxiogenic like effects in both experimental anxiety models (Kask et al., 1998a, b). Thus, in certain brain regions, there may be a tonic regulation of anxiety via NPY systems.

Interestingly, the levels of NPY in the CSF of patients with major depression were reduced as compared to non-depressed patients (Widerlov et al., 1986, 1988). Similarly, cortical tissues obtained form suicide victims with a medical history of depression revealed lower levels of NPY as compared to suicide victims with no reported depressive episodes (Widdowson et al., 1992). Higher levels of NPY in the CSF were found in depressed patients showing low symptoms of both psychological and somatic anxieties, while anxious patients had lower levels (Heilig and Widerlov, 1995). Most recently, lower plasma levels of NPY were reported in suicidal patients compared to healthy controls (Westrin et al., 1999). Taken together, these studies demonstrate that NPY is likely involved in anxiety-related behaviors in humans. However, at present, no pharmacological approaches are available to gain advantage of these beneficial effects of elevated NPY levels in anxiety-related disorders.

NPY, Seizures and Epilepsy

Having the similarities between NPY mediated effects and benzodiapines in mind, another important field for the treatment with benzodiazepines is their anti-convulsive property. Surprisingly, NPY deficient mice, despite otherwise largely normal phenotypes, exhibit spontaneous seizures (Erickson et al., 1996a, b), while exogenously administered NPY reduces the incidence and severity of kainic acid-induced seizures (Woldbye et al., 1997). Elevated NPY levels have been observed following limbic seizures, suggesting that it may have a protective effect against further seizure activity (Vezzani et al., 1996). Thus, another evolving role of NPY is found in neuronal excitability, and again, the parallelism with exogenous benzodiazepines is striking and the opposite effects to CRH-induced seizures (Ehlers et al., 1983) are apparent (Erickson et al., 1996; Vezzani et al., 1999).

In humans, temporal lob epilepsy is a neurological disorder in which the hippocampal formation is severely affected. In approximately two thirds of the cases, the hippocampus is often the only structure that shows pathological modifications (Amaral and Insausti, 1990). Considering that NPY-containing neurons degenerate in the hippocampus of patients with temporal lobe epilepsy (de Lanerolle et al., 1989) and that NPY regulates neuronal excitability in the rat hippocampus, the role of NPY and its receptors in humans certainly is critical. Thus, NPY and NPY receptor provide an important pharmacological target for the development of new anti-epileptic-like acting drugs. However, no compounds fulfilling pharmacological criteria for CNS targeting, peptide or receptor specificity and bioavailability are available at present.

NPY, Learning, Aging, Neurodegeneration with Cognitive Dysfunction

NPY and PYY enhance memory retention (Flood et al., 1989). The hippocampal Y2 receptor has been implicated in facilitating learning and memory processes with increases in memory retention induced by NPY (Flood et al., 1987). Passive immunization with NPY antibodies injected into the hippocampus induced amnesia (Flood et al., 1989). The hippocampal formation is associated with learning memory processes and is an area severely affected in Alzheimer's disease (Terry and Davies, 1980). Several studies have reported significant decreases in NPY-like immunoreactivity in cortical, amygdaloid and hippocampal areas in Alzheimer's disease brains (Chan-Palay et al., 1986b). Moreover, NPY binding sites are reduced in cortex and hippocampus of patients suffering from Alzheimer's disease (Martel et al., 1990). These data suggest that the degenerative process occurring in Alzheimer's disease may involve changes in NPY-related enervation. Interestingly, a major loss in NPY-like immunoreactive neurons has been reported in aged rats especially in cortical areas (Cha et al., 1996, 1997; Huh et al, 1997; 1998) and hypothalamic release of NPY is decreased in older rats (Hastings et al., 1998). The direct impact of NPY losses on cognitive behaviors in Alzheimer's disease remains to be established. Similar, in other neurodegenerative disorders such as Huntington's disease selective changes of NPY changes have been reported (Ferrante et al., 1987; Beal et al., 1986). At present, no treatment approaches have focussed on increasing NPY concentration in neurodegenerative disorders and/or other diseases states associated with cognitive dysfunction.

NPY, Opioid Withdrawal and Alcoholism

The expression of opioid withdrawal is thought to involve various brain regions (Koob et al., 1992). Early studies have suggested that exogenous application of NPY and related agonists could antagonize withdrawal by correcting deficits in NPY-like immunoreactivity at the levels of the hypothalamus (Pages et al., 1991). Recently, i.c.v. injections of NPY and related peptides have been shown to attenuated motor scores alterations induced by naloxone-precipitated withdrawal from morphine in rats (Woldbey et al., 1998). It remains to be established if similar data could be obtained in humans. Very recently, experimental studies have suggested that NPY, together with its receptors, may have direct implication in addiction to alcohol. NPY is involved in the Modulation of ethanol consumption and resistance. NPY-knockout mice were shown to have high ethanol consumption and low sensitivity to ethanol (Thiele et al., 1998). In contrast, mice overexpressing NPY drank much less alcohol than wild type and were also more sensitive to ethanol (Thiele et al., 1998). At present, no pharmacological approaches are available to gain advantage of these likely beneficial effects of elevated NPY levels in withdrawal and alcoholism.

NPY and Schizophrenia

Emerging evidence suggests that NPY might be involved in the pathophysiology of neuropsychiatric disorders (Wetstein et al., 1995). Region-specific decrease in NPY content has been described in patients with schizophrenia (Frederikson et al., 1991; Widerlov et al., 1988). Overactivity of mesolimbic dopaminergic pathways is believed to be of importance in drug reinforcement and schizophrenia (Beninger, 1983). There is evidence that some effects of NPY might be mediated via activation of dopamine (DA) receptors. First, a number of behavioral effects of NPY can be blocked by DA receptor antagonists (Moore et al., 1994; Josselyn and Beninger, 1993). Moreover, NPY has been shown to stimulate NMDA-stimulated DA release from rat striatum (Ault and Werling, 1997) and nucleus accumbens (Ault et al., 1998) providing direct evidence that NPY potentiates dopaminergic neurotransmission in these brain regions. Kask and Harro (2000) found that NPY Y1 receptor antagonism inhibits amphetamine-induced hyperactivity in rats and concluded that the ability of NPY Y1 receptor selective antagonists to modulate behavioral response to amphetamine an apomorhine suggests that NPY Y1 receptors may be involved in mediation of psychosis and reinforcement.

Neurological and Psychophysiological Effects of CNS NPY Systems: Pleiotropy

Thus, numerous studies have addressed the physiological functions of NPY and its congeners in the CNS (for reviews see: Kalra and Crowley, 1992; Dumont et al., 1992; Stanley, 1993; Wahlestedt and Reis, 1993; Grundemar et al, 1993; Gehlert, 1994, 1998; Colmers and Bleakman, 1994; Wetstein et al, 1995; Heilig and Widerlow, 1995; Munglani et al., 1996; Inui, 1999; Bischoff and Michel, 1999; Vezzani et al., 1999) and demonstrated a broad range of effects. This pleiotropy, together with its high degree of identity among mammalian species, suggests that NPY systems within the CNS are highly important pharmacological targets in various pathophysiological states. The peptide is involved in several neurological and psychophysiological processes, of which the anxiolytic-like, feeding, anti-convulsive and anti-addictive effects appear to be most prominent. These actions involve a site specific and a receptor specific action of NPY within the CNS. No pharmacological approaches exist, at present, to gain advantage of these various physiological functions.

Current Treatments of Anxiety Related Disorders Using Benzodiazepines

There are a number of new anxiolytic drugs that are fast acting and free from the unwanted side effects associated with the traditional benzodiazepines on the way toward the clinical development. Partial agonists at the benzodiazepine receptor, such as alpidem, abecamil and bretazenil, have highly promising preclinical profiles and some useful preliminary results in clinical testing of anxiety disorder subjects. Neurosteroids are another interesting set of pharmacologic agents that target the benzodiazepine receptor, have a preclinical anxiolytic profile and now need to be tested in clinical populations.

Neuropeptide receptor agonists and antagonists with anxiolytic properties may represent one of the most striking new classes of the potential anxiolytic drugs. As described above in detail, preclinical studies as well as clinical studies suggest that agonists of the neuropeptide Y receptors are provocative targets for anxiolytic agents (Kunovac & Stahl, 1995).

Current Problems in the Treatment of Anxiety Related Disorders Using Benzodiazepines or NPY The current methods for treatment of anxiety are accompanied by several problems:

The benzodiazepines that are commonly used as anxiolytic agents are unnatural compounds with a low or no selectivity. Beside their anxiolytic activity, the benzodiazepines show sedative and anti-epileptic effects and are suspected to influence muscle relaxation. Unfortunately, they are associated with a number of unwanted side effects, namely tiredness, sleepiness, lack of concentration, reduction of attentiveness and reactivity. Chronic application of benzodiazepines causes neurological disorders, like ataxia, dizziness, reflex loss, muscle and language disorders. A long-term treatment with benzodiazepines is predicted to entail dependency and addiction.

The direct i.c.v. administration of neuropeptide Y for the long-term treatment of anxiety in patients is not feasible.

SUMMARY OF THE INVENTION

It is an object of the present invention to provide the beneficial neurological and psychophysiological effects that result from the inhibition of DPIV-like enzymatic activity within the CNS. In addition, it is an object of the present invention to overcome or reduce the above stated problems with the prior art by providing a pharmacological approach that mimics a reduced DPIV-like enzymatic activity within the CNS and results in a delayed degradation of NPY or any other DPIV-like substrate. Further provided is one mechanism of action that—via an inhibition of the brain DPIV-like enzymatic activity—results in the magnification of endogenous neurological or neuropsychological effects mediated by NPY Y1 receptors, including but not limited to a reduction of anxiety. Also provided is a method of treating hypertension, fever, sleep dysregulation, anorexia, anxiety related disorders including depression, seizures including epilepsy, drug withdrawal and alcoholism, neurodegenerative disorders including cognitive dysfunction and dementia, and neuropsychiatric disorders including schizophrenia diagnosed in a subject, compromising administering to the subject a CNS targeted DPIV inhibitor via oral, parenteral or any other route of administration.

DETAILED DESCRIPTION OF THE INVENTION

Figure 1:
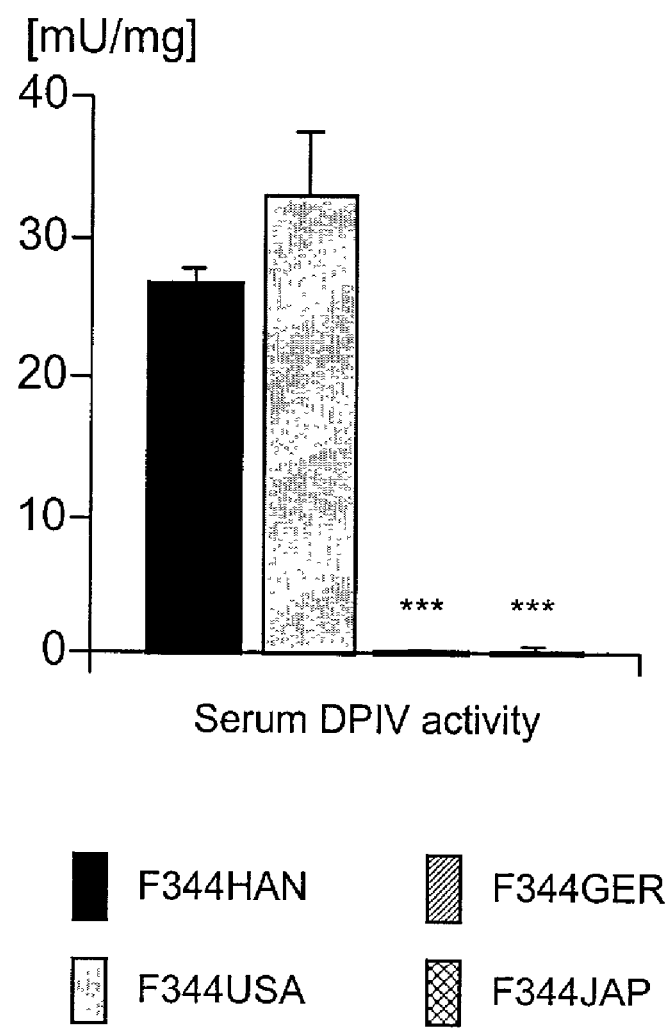
FIG. 1 shows the DPIV enzymatic activity in serum of Fischer 344 (F344) rat substrains from Hannover (HAN), United States (USA), German (GER) and Japanese (JAP) breeders. The results are mean (±SEM) of 4–5 age-matched animals per genotype. Analysis of variance revealed a significant effect of "substrain" with F(3, 15): 50.4, p<0.0001. Asterisks indicate significant PLSD post hoc effects vs. "wild-type" F344USA and F344HAN substrains ("***"=p<0.0001).

In contrast to other proposed methods in the art, the present invention provides an orally available therapy with low molecular weight inhibitors of dipeptidyl peptidase IV. The instant invention represents a novel approach for the treatment of anxiety and other neurological or psychological disorders. It is user friendly, commercially useful and suitable for use in a therapeutic regime, especially concerning human disease.

Examples for orally available low molecular weight dipeptidyl peptidase IV inhibitors are agents such as, N—(N'-substituted glycyl)-2-cyanopyrrolidines, L-threo-isoleucyl thiazolidine, L-allo-isoleucyl thiazolidine, L-threo-isoleucyl pyrrolidine, L-allo-isoleucyl thiazolidine, and L-allo-isoleucyl pyrrolidine. They are described in U.S. Pat. No. 6,001,155, WO 99/61431, WO 99/67278, WO 99/67279, DE 198 34 591, WO 97/40832, DE 196 16 486 C 2, WO 98/19998, WO 00/07617, WO 99/38501, and WO 99/46272, the teachings of which are herein incorporated by reference in their entirety. The goal of these agents is to inhibit DPIV, and by doing so, to lower blood glucose levels thereby effectively treating hyperglycemia and the attendant disease associated with elevated levels of glucose in the blood.

DPIV is an enzyme that is an exopeptidase, which selectively cleaves peptides after penultimate N-terminal proline and alanine residues. Endogenous substrates for this enzyme include the incretins, such as glucose-dependent insulinotropic polypeptides, like GIP and GLP-1. In the presence of DPIV, these hormones are enzymatically reduced to inactive forms. The inactive form of GIP and GLP cannot induce insulin secretion, thus blood glucose levels are elevated, especially in the hyperglycemic state. Elevated blood glucose levels have been associated with many different pathologies, including diabetes mellitus (Type 1 and 2) and the sequel accompanying diabetes mellitus.

It has also been discovered that DPIV plays a role in T-cell-mediated immune responses, for example, in organ transplantation. Inhibition of DPIV has been demonstrated to prolong cardiac allografts. Additionally, the inhibition of DPIV has contributed to the suppression of rheumatoid arthritis. DPIV has also been attributed a role in HIV's penetration into T-cells (T-helper cells).

These various effects of dipeptidyl peptidase IV inhibitors imply their impact on normal healthy tissues and organs, when they are used for the treatment of a pathologically altered tissue. The goal of the present invention is the development of highly selective brain targeted dipeptidyl peptidase IV inhibitors, which display a high bioavailability and an exactly predictable activity time in the target tissue.

Examples for target specific, orally available low molecular weight agents are prodrugs of stable and unstable dipeptidyl peptidase IV inhibitors which comprise general formula A-B-C, whereby A represents an amino acid, B represents the chemical bond between A and C or an amino acid, and C represents an unstable or a stable inhibitor of dipeptidyl peptidase IV respectively. They are described in WO 99/67278, WO 99/67279 the teachings of which are herein incorporated by reference in their entirety.

The present invention relates to a novel method in which the reduction of activity in the enzyme dipeptidyl peptidase (DPIV or CD 26) or of DPIV-like enzyme activity in brain of mammals induced by effectors of the enzyme leads as a causal consequence to a reduced degradation of the neuropeptide Y (NPY) by DPIV and DPIV-like enzymes. Such treatment will result in a reduction or delay in the decrease of the concentration of functional active NPY (1–36).

As a consequence of the resulting enhanced stability of the endogenous NPY (1–36) caused by the inhibition of DPIV activity, NPY activity is prolonged resulting in functionally active NPY Y1 receptor activity facilitating—among others—anti-depressive, anxiolytic and anti-hypertensive effects (see above).

The method of the present invention for treating anxiety in an animal, including humans, in need thereof, comprises potentiating NPY's presence by inhibiting DPIV, or related enzyme activities, using an inhibitor of the enzyme. Oral administration of a DPIV inhibitor may be preferable in most circumstances. By inhibiting the DP IV enzyme activity, the half-life of the active form of NPY will be appreciably extended and maintained under physiological conditions. The extended presence of active NPY will enhance the NPY Y1 receptor activity.

This invention also provides pharmaceutical compositions. Such compositions comprise a therapeutically (or prophylactically) effective amount of the inhibitor (and/or a sugar pill to accompany administration of a DPIV inhibitor), and a pharmaceutically acceptable carrier or excipient. Suitable carriers include but are not limited to saline, buffered saline, dextrose, water, glycerol, ethanol, and combinations thereof. The carrier and composition are preferably produced under good laboratory practices conditions and most preferably are sterile. The formulation is ideally selected to suit the mode of administration, in accordance with conventional practice.

Suitable pharmaceutically acceptable carriers include but are not limited to water, salt solutions (for example, NaCl), alcohols, gum arabic, vegetable oils, benzyl alcohols, polyethylene glycols, gelatin, carbohydrates such as lactose, amylose or starch, magnesium stearate, talc, viscous paraffin, perfume oil, fatty acid esters, hydroxymethylcellulose, polyvinyl pyrrolidone, etc. The pharmaceutical preparations can be sterilized and if desired mixed with auxiliary agents, for example, lubricants, preservatives, stabilizers, wetting agents, emulsifiers, salts for influencing osmotic pressure, buffers, coloring, flavoring and/or aromatic substances and the like which do not deleteriously react with the active compounds, but which improve stability, manufacturability and/or aesthetic appeal.

The compositions, if desired, can also contain minor amounts of wetting or emulsifying agents, or pH buffering agents. In addition, the composition can be a liquid solution, suspension, emulsion, tablet, pill, capsule, sustained release formulation, or powder. In addition, the composition can be formulated as a suppository, with traditional binders and carriers such as triglycerides. Oral formulations can include standard carriers such as pharmaceutical grades of mannitol, lactose, starch, magnesium stearate, polyvinyl pyrrolidone, sodium saccharine, cellulose, magnesium carbonate etc.

Further, the compositions can be formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active compound. Where the composition is to be administered by infusion, it can be dispensed with an infusion bottle containing sterile pharmaceutical grade water, saline or dextrose/water. Where the composition is administered by injection, an ampoule of sterile water for injection or saline can be provided so that the ingredients may be mixed prior to administration.

Finally, compositions of the invention can be formulated as neutral or salt forms. Pharmaceutically acceptable salts include those formed with free amino groups such as those derived from hydrochloric, phosphoric, acetic, oxalic, tartaric acid, etc., and those derived from sodium, potassium, ammonium, calcium, ferric hydroxides, isopropylamine, triethylamine, 2-ethylamino ethanol, histidine, procaine, etc.

The amount of the invention's composition which will be effective in the treatment of a particular disorder or condition will depend on the nature of the disorder or condition, and can be determined by standard clinical techniques. In addition, in vitro and/or in vivo assays may optionally be employed to help identify optimal dosage ranges. The precise dose to be employed in the formulation will also depend on the route of administration, and the seriousness of the disease or disorder, and should be decided according to the judgement of the practitioner and each patient's circumstances.

It will be readily understood by the skilled artisan that numerous alterations may be made to the examples and instructions given herein including the generation of different DP IV inhibitors and alternate therapeutic compositions without departing from either the spirit or scope of the present invention.

The present invention will now be illustrated with reference to the following examples focussing on the anxiolytic-like and stress-protective-like action of reduced DPIV-like activity in a genetic model of DPIV deficiency (example 1), the anxiolytic-like action of pharmacologically induced DPIV inhibition within the CNS (example 2), the interaction and potentiation of NPY mediated anxiolytic-like effects (example 3), and the characterization of an anxiolytic-like mechanism compromising DPIV-inhibition and resulting potentiation of NPY Y1 receptor mediated effects (Example 4).

EXAMPLES OF THE INVENTION

Example 1

Spontaneous mutations of the DPIV gene observed in substrains of Fischer (F344) rats provide a model for studying the role of DPIV in behavioral regulation and adaptation to stress. The mutations in F344 rats result in a lack of DPIV-like enzymatic activity and are found in substrains from Germany (GER) and Japan (JAP) (Thompson et al., 1991; Tsuji et al., 1992) while rats from US (USA) and Hannover (HAN) breeders show significant enzyme activity. In F344JAP rats, a G633R substitution in the CD26 protein causes a greatly reduced expression of a mutant inactive enzyme (Tsuji et al., 1992; Cheng et al., 1999) while the other DPIV negative F344GER substrain expresses a non-active mutant enzyme (Thompson et al., 1991). The F344JAP rat is therefore be considered as an "protein knock-out" model (Cheng et al., 1999) while the F344GER substrain may represent a "protein over-expression" model (Shingu, Helfritz, Meyer, Schmidt, Mentlein, von Hörsten, submitted). On the basis of these findings, a direct comparison of mutant F344JAP and F344GER substrains with "wild-type" F344USA rats would allow the differentiation between the role of DPIV expression and activity on behavioral regulation and other neurological and psychophysiological functions in vivo. In the present example we report that DPIV deficient F344 substrains are less anxious and less responsive to stress-induced physiological changes.

Animals. F344USA, F344JAP and F344GER substrains were obtained from the different countries via Charles River Germany. F344Han rats, initially derived from the F344USA substrain, were obtained from a breeding colony at the Central Animal Laboratory at Hannover Medical School. All substrains were bred for one generation at the Central Animal Laboratory at Hannover and maintained in a specific-pathogen-free facility at 25° C. under a 12 h light-12 h dark cycle (light on at 0700 h), with ad libitum access to food and water. For the experiments age-matched weeks old F1 offspring of all substrains was used. The District Government, Hannover, Germany, approved all research and animal care procedures.

Quantification of DPIV activity in tissue of F344 substrains. Plasma, lung and various other tissue samples were kept frozen at −80° C. until use. Tissue was homogenized and DPIV enzyme activity was detected by incubating the substrate, glycylproline p-nitroanilide (gly-Pro-pNA, 1 mg/ml in PBS) (Bachem, Germany), and the color development was measured at 405 nm.

Social interaction (SI) test. The SI test was carried out as first described by File (1980) and has initially been validated in the laboratory (Kask, Nguyen, Pabst, von Hörsten, submitted). Two rats, matched for genotype and body weight, were removed from home cages and exposed to the testing environment. The arena was a squared open field (50×50×50 cm) made of aluminum, placed inside a sound isolation box (Coulboum Instruments, Lehigh Valley, Pa.). For details of the apparatus see our previous study (von Hörsten et al., 1998c). The open field was lit by a red photo light bulb (Philips PF712E; 1.3 Lux). Rats were unfamiliar with the apparatus. Behavior was monitored using a video camera placed above the field inside the testing/isolation box. The SI behavior of both rats was recorded on-line from a monitor placed outside on top of the box. The following parameters were scored by an observer (HPN) unaware of the substrain of rats: duration of time spent in sniffing, following, crawling under and over other rats, but not passive body contact (resting, sleeping). An increase of the SI time is considered an anxiolytic-like response.

Stress induced body weight loss. On three consecutive days, age matched animals from Japanese (JAP), United States (USA) and German (GER) breeders were individually transported to a novel room and remained there for 1 h. On the first day a novel cage containing sawdust was used and animals placed in a standard animal rack. On the second day procedure was the same except that the cage was without sawdust. The stress procedure on the third was the same as on day 2 except that the cage was placed on the bottom of the novel room.

Statistical analysis. Data from repeated observations were analyzed by two-way analyses of variance for repeated measures (ANOVA) (factors: "substrain" and "change of body weight after stress" as repeated measure). Data obtained from simple measures such as DPIV activity or SI time were analyzed by one-way (factor: "substrain") ANOVA. Asterisks indicate significant post hoc effects vs. F344USA substrain (Control) obtained by Fisher's PLSD. All data are presented as means±S.E.M.

DPIV activity in F344 substrains. Corresponding to the literature, F344GER and F344JAP substrains lack endogenous DPIV activity (FIG. 1). Thus, these rats provide a genetic model for the investigation of the physiological role of DPIV activity in behavioral regulation.

Figure 2:
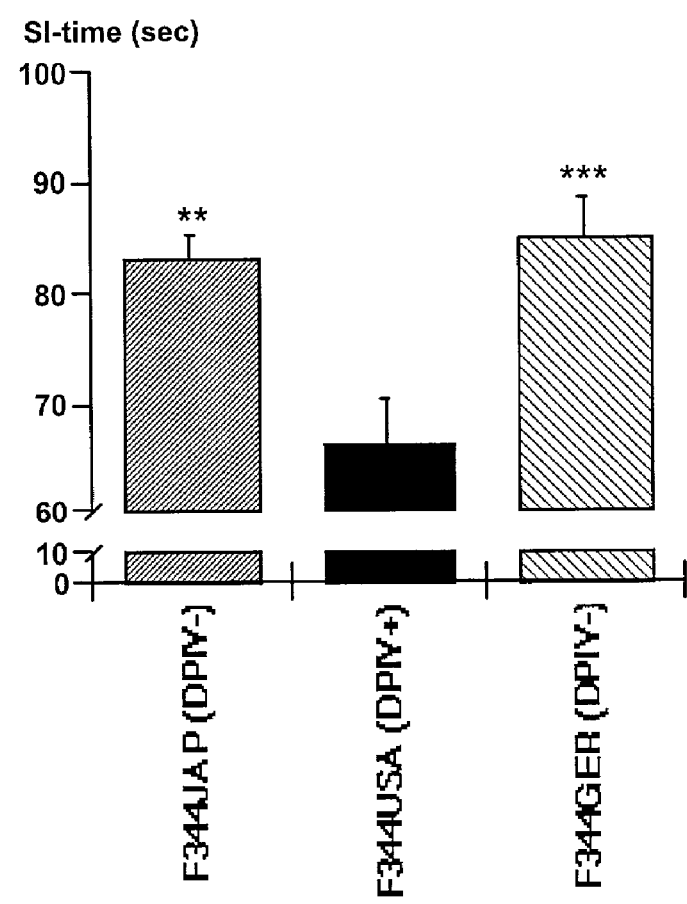
FIG. 2 shows the time spent in active social interaction (SI) time in Fischer 344 (F344) rat substrains from Japanese (JAP), United States (USA) and German (GER) breeders. F344JAP and F344GER rats are mutant for the enzymatic function of dipeptidyl-peptidase IV (DPPIV) and lack endogenous DPPIV activity (see also FIG. 1). F344JAP rats provide a "protein knock-out" model because DPPIV is markedly reduced expressed on cell surface (Tsuji et al., 1992; Cheng et al., 1999). F344GER rats express a mutant non-enzymically active DPPIV-like protein (Thompson et al., 1991). An increase of the SI time in the rat social interaction test of anxiety is interpreted as an anxiolytic-like response. The results are mean (±SEM) of 12 age-matched animals per genotype. Analysis of variance revealed a significant effect of "substrain" with F(2, 32): 8.8, p=0.0009. Asterisks indicate significant PLSD post hoc effects vs. "wild-type" F344USA rats (""=p<0.01; "*"=p<0.001).

Anxiety in the social interaction test: Those F344 substrains that lack DPIV activity (F344JAP and F344GER) spent significantly more time in active social interaction with a novel arena (FIG. 2). Thus, the lack of endogenous DPIV-like activity mediates anxiolytic-like effects.

Figure 3:
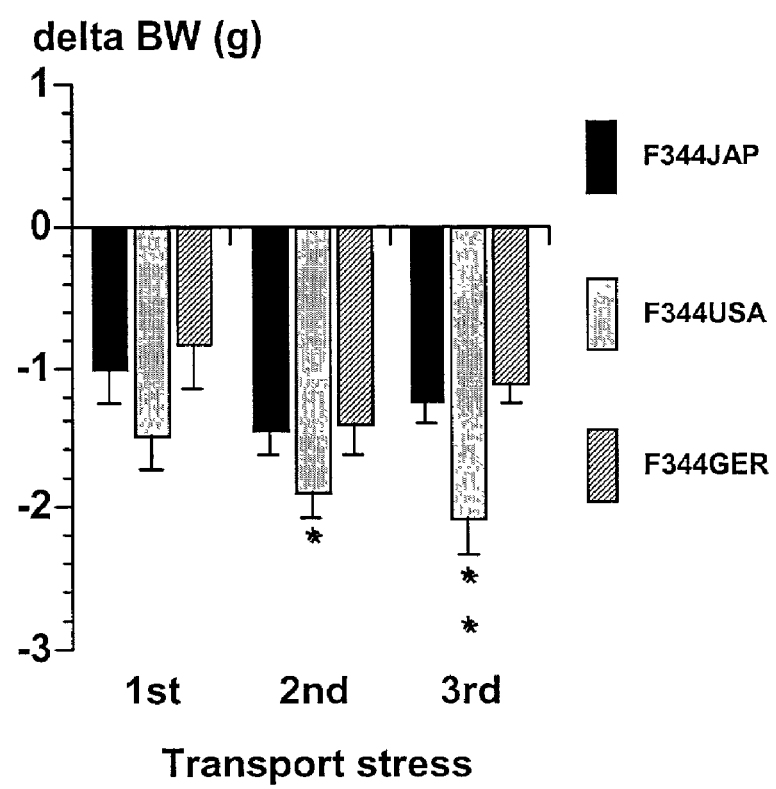
FIG. 3 shows the change of body weight after stress on three consecutive days. On three consecutive days, age matched animals from Japanese (JAP), United States (USA) and German (GER) breeders were individually transported to a novel room and remained there for 1 h. On the first day a novel cage containing sawdust was used and animals placed in a standard animal rack. On the second day procedure was the same except that the cage was without sawdust. The stress procedure on the third was the same as on day 2 except that the cage was placed on the bottom of the novel room. Analysis of variance for repeated measures revealed a significant effect of "substrain" with F(2, 30): 13.5, p=0.0004. Asterisks indicate significant PLSD post hoc effects one factor ANOVAs split by day vs. "wild-type" F344USA ("*" p<0.05; "**"=p<0.01).

Stress-induced body-weight loss: F344JAP and F344GER lose significantly less body weight after repeated 1 h transport stress. Thus, the lack of endogenous DPIV-like activity in these substrains reduces the physiological changes induced by moderate stress (FIG. 3).

Together, these data demonstrate that in the genetic model of the DPIV deficient F344 rats the lack of endogenous DPIV activity cause anxiolytic-like and stress-protective effects. The pharmacological simulation of DPIV deficiency, i.e. DPIV inhibitor treatment, may therefore cause anxiolytic-like effects (see example 2).

Example 2

In the previous example we have demonstrated that anxiety and stress-responsiveness were reduced in a genetic model of DPIV deficiency. In the present example, we report that central administration (i.c.v.) of the DPIV selective inhibitor P32/98 leads to anxiolytic-like effects in a well-established test of anxiety in rodents, the elevated plus maze test. We further report that also the emotionality of rats in response to novelty as measured by the open field paradigm (Denenberg et al., 1968) is less pronounced in P32/98 treated rats without affecting activity.

Animals. Male WistarF/Han (WF) rats (Central Animal Laboratory, Hannover Medical School, Hannover, Germany, weighing 350–390 g, were housed in a sound-proof, temperature controlled (24.0±0.5° C.) room under specific pathogen free conditions with a 12/12 h dark/light cycle (lights on at 07.00 with illumination level of 80 Lux). Food (Altromin lab chow pellets) and tap water were available ad libitum. Under ketamine/xylasine (100/5 mg/kg, i.p.) anesthesia, the rats were fixed in a Kopf stereotaxic frame and implanted with cannulae (Plastic One, Inc., Roanoke, Va., USA) above the lateral ventricle. All research and animal care procedures were approved by the Lower Saxony district government (Hannover, Germany) and followed principles described in the European Community's Council Directive of 24 Nov. 1986 (86/609/EEC).

Surgery and i.c.v. application. For surgery, rats were anesthetized and prepared with i.c.v. cannulaes (coordinates: A: −0.7 mm caudal, L: 1.4 mm lateral to bregma; and V: 3.2 mm ventral to the skull surface; tooth bar +3.0 above ear bars) using standard stereotaxic procedures as described in detail elsewhere (von Hörsten et al., 1998a, b, c). After a 7-day recovery period, successful ventricle cannulation was confirmed by an angiotensin drinking response (von Hörsten et al., 1998a). Rats showing a positive drinking response (n=40) were then habituated to experimental handling by daily sham injections for seven days.

Animals were randomly divided into four experimental groups (n—8–10/group), which completed different behavioral tests of experimental anxiety. Animals in each group were treated in an identical way in each phase, receiving i.c.v. injections −60 mins before behavioral testing: Artificial cerebrospinal fluid (aCSF) (Control), P32/98 (0.05 nmol), P32/98 (5 nmol) and P32/98 (500 nmol). P32/98 was adjusted to the final concentration using buffered aCSF and applied in a volume of 5 µl/min into the right lateral ventricle. The cannula was attached to a Hamilton microsyringe with approximately 30 cm of polyethylene tubing and all compounds were infused at a rate of 5.0 µl/min using a TSE multichannel infusion pump (Bad Homburg, Germany).

Response to novelty (Open field test). Differences in the response to novelty induced by central DPIV antagonism were studied using an open field (OF) test. The general procedure has been described elsewhere in detail (von Hörsten et al., 1993, 1998d). However, the following modifications were applied: During the dark phase, rats were placed in a squared 50×50 cm OF within a sound isolated box illuminated by red photo light. Spontaneous activity during a single continuous test session of 15 min was recorded using a video path analyzer system (E61–21 Video Path Analyser system, Coulboum instruments, PA, U.S.A.). The analyzer system determines behavior at 15 one min intervals, analyzing 14 data elements: Wall-, corner-, quadrant 1–4-, locomotion-, rest-, and rearing-time (all in sec.), stereo-, rearing-, rotation clockwise- and counterclockwise-events (all integers), and distance traveled (cm). Furthermore, the total incidence of fecal boli was counted after each session and the incidence and duration (sec) of grooming behavior was simultaneously recorded from a video monitor by a person blind to the treatment of the animals (von Hörsten et al., 1998c).

Elevated plus maze (EPM) testing. The elevated plus maze apparatus and the test procedure were adapted according to Fernandes and File 1996 based on general considerations and validation for use with rats. The E+apparatus (TSE Systems, Bad Homburg, Germany) was made of gray plastic and had two open arms (50×10 cm) and two enclosed arms of the same size with walls 40 cm high, elevated 50 cm above the ground. The maze was equipped with light beam sensors that enabled computerized measurement of E+ performance. The maze was lit with red light bulb (Philips PF712E; 1.5 Lux) placed 30 cm above maze in a way that closed arms remained in the shadow. At start of experiment the rat was placed on central platform (10×10 cm), with its head facing the closed arm, and allowed to freely explore the maze for 5 min. The following parameters were calculated: Total numbers of arm entries (TA); entries to closed arms (CA); entries to open arms (OA); percentage frequency of entries to open arms (% OA: OA×100/TA); total trial duration (TT): 300 s; duration of stay in closed arms (closed time; CLT); percentage share of CLT in total arms-stay duration (CLT×100/AT); duration of stay in open arms (open time; OT) and percentage share of OT in total arm-stay duration (% OT: OT×100/AT). In addition to the standard spatiotemporal measurements, "time spent and percentage of time on the central square" were recorded (center time, CT: duration of stay on platform in seconds; percentage share of CT in trial duration, % CT: CT×100/TT). An increase of the time spent on the open arms is interpreted as an anxiolytic response, a decrease of this parameter an anxiogenic response, whereas the number of entries into closed arms provides an indication of general activity (Pellow et al., 1985).

Statistical analysis. For statistical analysis, behavioral raw data from every test minute were analyzed by two-way analyses of variance (ANOVA) for repeated measures (factors: treatment and time as a repeated measurement). Data obtained as totals from a session were analyzed by one-way (factor: treatment) ANOVA. Significant post hoc effects vs. aCSF (Control) obtained by Fisher's PLSD are indicated by an asterisk. All data are presented as means ±S.E.M.

Figure 4:
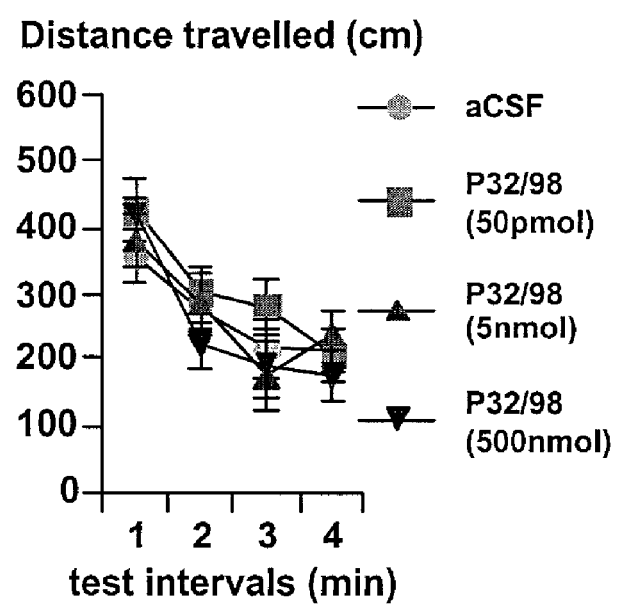
FIG. 4 shows the effect of i.c.v. P32/98 treatment on the distance traveled in four consecutive minutes of open field testing. Analysis of variance for repeated measures revealed no significant effect of treatment on this parameter of activity (F(3, 78): 0.7, p=0.5; n.s.).
Figure 5:
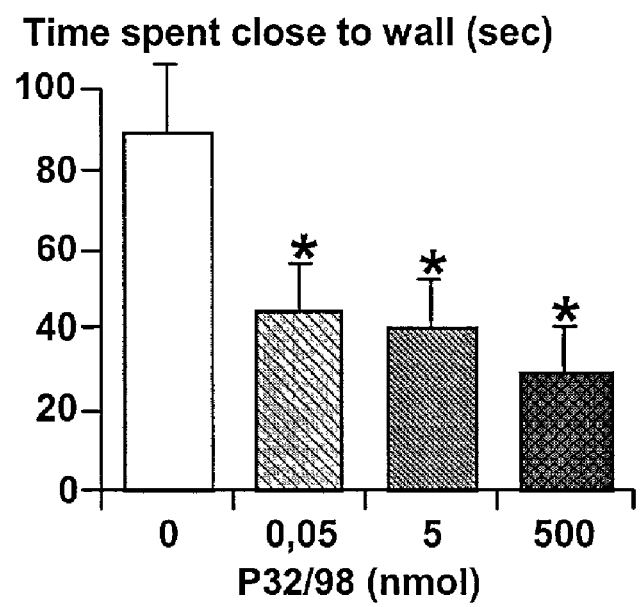
FIG. 5 shows the effect of i.c.v. P32/98 treatment on the time spent close to the wall as a sum of four consecutive minutes of open field testing. Analysis of variance revealed a significant effect of "treatment" with F(3, 26): 4.1, p=0.015. Asterisks indicate significant PLSD post hoc effects vs. "aCFS" controls ("*"=p<0.05).

Response to P32/98 in the open field: P32/98 had no effect on activity in the open field in a wide range of dosages (FIG. 4). As on characteristic of reduced emotionality in the open field, there was a dose-dependent reduction of the time spent close to the wall induced by P32/98 (FIG. 5). Very low dosage of 50 pmol was already effective.

Figure 6:
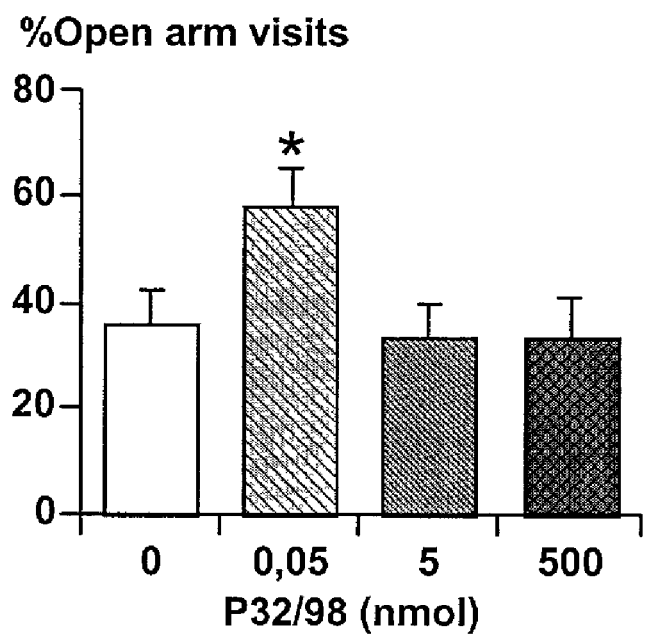
FIG. 6 shows the effect of i.c.v. P32/98 treatment on the percentage of time spent on the open arms of the elevated plus maze (EPM). Analysis of variance revealed a significant effect of "treatment" with F(3, 26): 3.0, p=0.048. Asterisks indicate significant PLSD post hoc effects vs. "aCFS" controls ("*"=p<0.05).

Response to P32/98 in the EPM: P32/98 at low dose (50 pmol) increased the percentage of time spent on the open arms of the maze being indicative for an anxiolytic-like effect (FIG. 6). Together, these data indicate for the first time that the specific pharmacological inhibition of CNS DPIV systems produces dose dependent anxiolytic-like effects in two animal models of anxiety.

Example 3

In the previous examples we have demonstrated that anxiety and stress-responsiveness were reduced in a genetic model of DPIV deficiency. We further have shown that pharmacological inhibition of CNS DPIV systems results in dose-dependent anxiolytic-like effects in the plus maze and open field paradigms of experimental anxiety. In the present example, we report that central administration (i.c.v.) of the DPIV selective inhibitor P32/98 itself has also dose-dependent anxiolytic-like effects in the social interaction test of anxiety. We also report that the magnitude of anxiolysis by P32/98 is similar to that produced by NPY. In addition, we show that combined application of P32/98 and NPY has additive anxiolytic-like effects in the SI test. Finally, we show that 1 h and 12 h food intake is less affected by P32/98 treatment alone and in combinations.

Animals. Male WistarF/Han (WF) rats (Central Animal Laboratory, Hannover Medical School, Hannover, Germany, weighing 330–370 g, were housed in a sound-proof, temperature controlled (24.0±0.5° C.) room under specific pathogen free conditions with a 12/12 h dark/light cycle (lights on at 07.00 with illumination level of 80 Lux). Food (Altromin lab chow pellets) and tap water were available ad libitum. Under ketamine/xylasine (100/5 mg/kg, i.p.) anesthesia, the rats were fixed in a Kopf stereotaxic frame and implanted with cannulae (Plastic One, Inc., Roanoke, Va., USA) above the lateral ventricle. All research and animal care procedures were approved by the Lower Saxony district government (Hannover, Germany) and followed principles described in the European Community's Council Directive of 24 Nov. 1986 (86/609/EEC).

Surgery and i.c.v. application. For surgery, rats were anesthetized and prepared with i.c.v. cannulae (coordinates: A: −0.7 mm caudal, L: 1.4 mm lateral to bregma; and V3.2 mm ventral to the skull surface; tooth bar +3.0 above ear bars) using standard stereotaxic procedures as described in detail elsewhere (von Hörsten et al., 1998a, b, c). After a 7-day recovery period, successful ventricle cannulation was confirmed by an angiotensin drinking response (von Hörsten et al., 1998a). Rats showing a positive drinking response (n=59) were then habituated to experimental handling by daily sham injections for seven days.

Animals were randomly divided into two sets of four experimental groups (n=5–6/group), which completed different consecutive SI test of anxiety. Animals in each group were treated in an identical way in each phase, receiving i.c.v. injections −60 mins and −45 min before behavioral testing with different dosages (P32/98: 5 pmol–500 nmol; NPY: 50 pmol–1.6 nmol). P32/98 was adjusted to the final concentration using buffered aCSF and applied in a volume of 5 μl/min into the right lateral ventricle. The cannula was attached to a Hamilton microsyringe with approximately 30 cm of polyethylene tubing and all compounds were infused in a total volume of 5.0 μl at a rate of 5.0 μl/min using a TSE multichannel infusion pump (Bad Homburg, Germany). The time spent in active social interaction (SI-time), 1 h and 12 h food-intake were measured. Animals were repeatedly tested with randomly chosen treatment and always-new interaction partners. Tests were separated with at least 4 days from each other and always conducted in the dark cycle. Five tests series were performed. Each test, spanning four groups (aCSF+aCSF; aCSF+NPY; P32/98+aCSF; P32/98+NPY) of 5–6 animals per condition.

Social interaction (SI) test. The SI test was carried out as first described by File (1980) and has initially been validated in the laboratory (Kask, Nguyen, Pabst, von Hörsten, submitted). Two rats, matched for genotype and body weight, were removed from home cages and exposed to the testing environment. The arena was a squared open field (50×50×50 cm) made of aluminum, placed inside a sound isolation box (Coulbourn Instruments, Lehigh Valley, Pa.). For details of the apparatus see our previous study (von Hörsten et al., 1998c). The open field was lit by a red photo light bulb (Philips PF712E; 1.3 Lux). Rats were unfamiliar with the apparatus. Behavior was monitored using a video camera placed above the field inside the testing/isolation box. The SI behavior of both rats was recorded on-line from a monitor placed outside on top of the box. The following parameters were scored by an observer (HPN) unaware of the substrain of rats: duration of time spent in sniffing, following, crawling under and over other rats, but not passive body contact (resting, sleeping). An increase of the SI time is considered an anxiolytic-like response.

Statistical analysis. Data from repeated observations (food intake) were analyzed by two-way analyses of variance for repeated measures (ANOVA) (factors: "substrain" and "food intake" as repeated measure). Data obtained from simple measures such as DPIV activity or SI time were analyzed by one-way (factor: "substrain") ANOVA. Asterisks indicate significant post hoc effects vs. aCSF+aCSF (Control) obtained by Fisher's PLSD. All data are presented as means±S.E.M.

Figure 7:
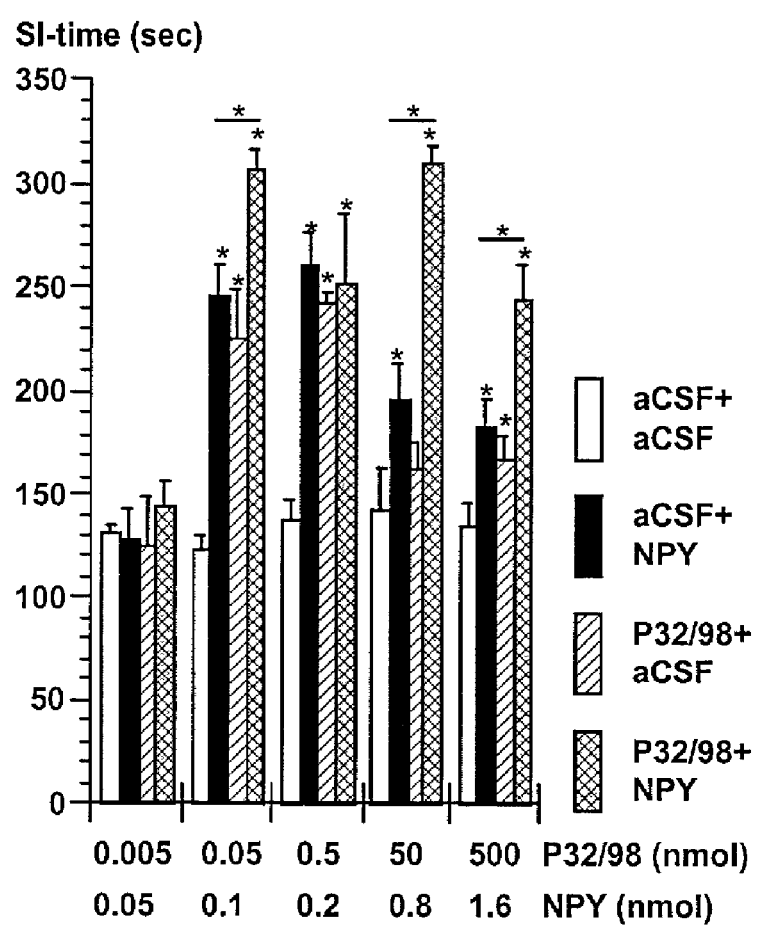
FIG. 7 shows the effect of combined i.c.v. treatment using aCSF, P32/98 and NPY in combinations at different dosages (P32/98: 5 pmol–500 nmol; NPY: 50 pmol–1.6 nmol). The time spent in active social interaction (SI-time) in the social interaction test of anxiety was measured. An increase of the SI-time is indicative for an anxiolytic like effect. After habituation to the testing procedure animals were repeatedly tested with randomly chosen treatment and always-new interaction partners. Tests were separated with at least 4 days from each other. For each test, spanning four groups of 5–6 animals per condition, analysis of variance revealed the following significant effects of "treatment" (aCSF+aCSF; aCSF+NPY; P32/98+aCSF; P32/98+NPY) from left to right: P32/98 5 pmol+NPY 50 pmol: F(3, 18): 0.25, p=0.8, n.s.; P32/98 50 pmol+NPY 100 pmol: F(3, 18): 22.4, p<0.0001; P32/98 500 pmol+NPY 200 pmol: F(3, 20): 8.6, p=0.007; P32/98 50 nmol+NPY 0.8 nmol: F(3, 20): 23.3, p<0.0001; and P32/98 500 nmol+NPY 1.6 nmol: F(3, 20): 11.2, p=0.0008. Asterisks indicate significant PLSD post hoc effects vs. "aCFS+aCSF" controls and as indicated by bars between aCSF+NPY vs. P32/98+NPY ("*"=p<0.05).

Dose dependent anxiolysis in the SI test by P32/98. Central administration of the DPIV selective inhibitor P32/98 (group: aCSF+P32/98: 5 pmol–500 nmol) produced "bell-shaped" dose-dependent anxiolytic-like effects in the social interaction test of anxiety (FIG. 7). This demonstrates that P32/98 acts also in the SI test as a potent anxiolytic-like compound—similar to the EPM and the open field tests (see example 2). I.c.v. application of NPY (0.05–1.6 nmol) had a similar anxiolytic-like effect (FIG. 7). This finding replicates the known anxiolytic-like action of NPY, as described in the background art. The comparison of P32/98-mediated effects with those of NPY indicates that the inhibitor is of similar potency. Interestingly, pretreatment of P32/98 followed by NPY produced an additive effect over a wide range of dosages (FIG. 7), suggesting that these compounds act through the same mechanism. As described in the prior art, this mechanisms is most probably the activation of CNS Y1 receptors.

Figure 8:
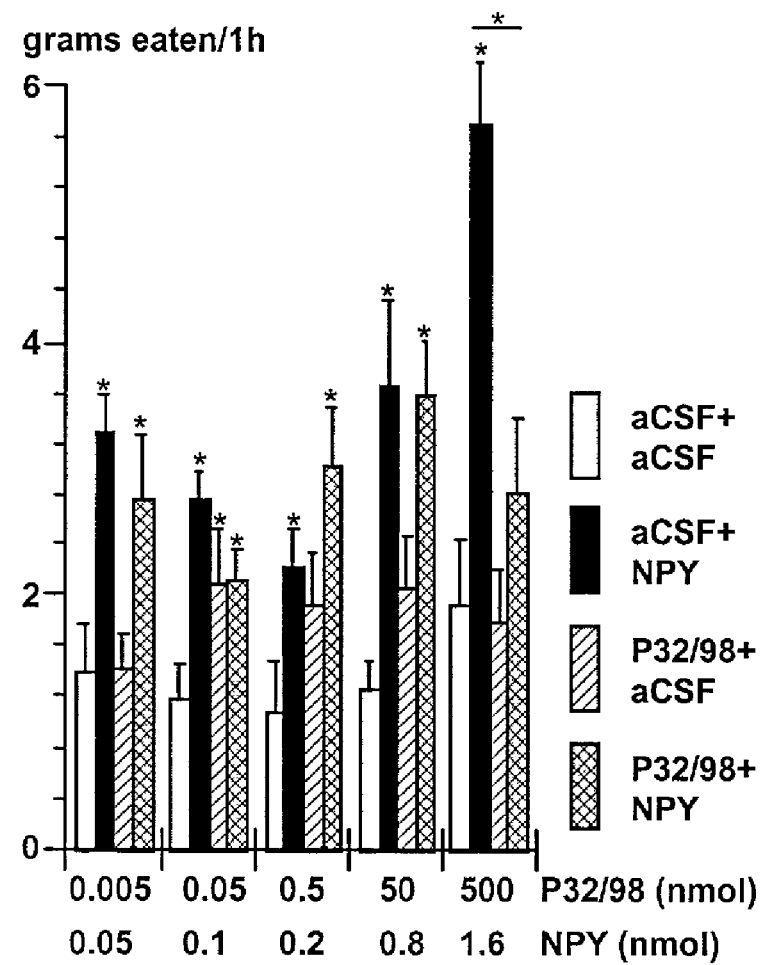
FIG. 8 shows the effect of combined i.c.v. treatment using aCSF, P32/98 and NPY in combinations at different dosages (P32/98: 5 pmol–500 nmol; NPY: 50 pmol–1.6 nmol). The amount of food eaten within 1 h was measured. Animals were repeatedly tested with randomly chosen treatments. Tests were separated with at least 4 days from each other. For each test, spanning four groups of 5–6 animals per condition, analysis of variance revealed the following significant effects of "treatment" (aCSF+aCSF; aCSF+NPY; P32/98+aCSF; P32/98+NPY) from left to right: P32/98 5 pmol+NPY 50 pmol: F(3, 18): 7.0, p=0.0025; P32/98 50 pmol+NPY 100 pmol: F(3, 20): 4.5, p=0.016; P32/98 500 pmol+NPY 200 pmol: F(3, 20): 4.4, p=0.015; P32/98 50 nmol+NPY 0.8 nmol: F(3, 20): 6.6, p=0.0027; and P32/98 500 nmol+NPY 1.6 nmol: F(3, 20): 13.7, p<0.0001. Asterisks indicate significant PLSD post hoc effects vs. "aCFS+aCSF" controls and as indicated by bars between aCSF+NPY vs. P32/98+NPY ("*"=p<0.05).
Figure 9:
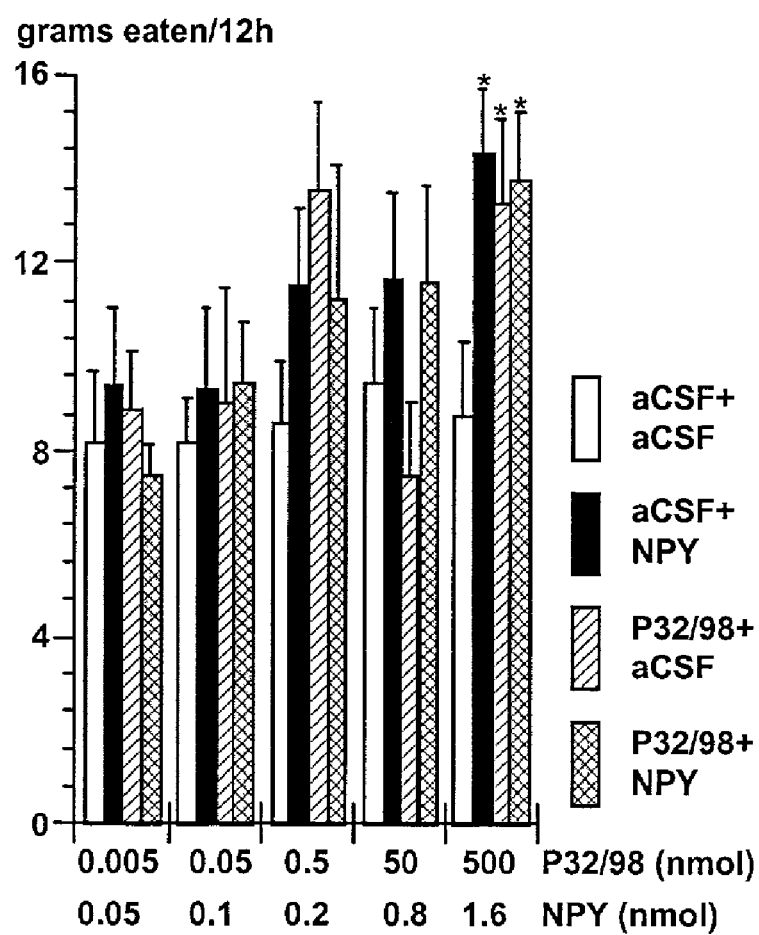
FIG. 9 shows the effect of combined i.c.v. treatment using aCSF, P32/98 and NPY in combinations at different dosages (P32/98: 5 pmol–500 nmol; NPY: 50 pmol–1.6 nmol). The amount of food eaten within 12 h was measured. For each test, spanning four groups of 5–6 animals per condition, analysis of variance revealed the following significant effects of "treatment" (aCSF+aCSF; aCSF+NPY; P32/98+aCSF; P32/98+NPY) from left to right: P32/98 5 pmol+NPY 50 pmol: F(3, 18): 0.5, p=0.7, n.s.; P32/98 50 pmol+NPY 100 pmol: F(3, 20): 0.17, p=0.9, n.s.; P32/98 500 pmol+NPY 200 pmol: F(3, 20): 1.1, p=0.34, n.s.; P32/98 50 nmol+NPY 0.8 nmol: F(3, 20): 1.2, p=0.3; and P32/98 500 nmol+NPY 1.6 nmol: F(3, 20): 3.4, p=0.039. Asterisks indicate significant PLSD post hoc effects vs. "aCFS+aCSF" controls and as indicated by bars between aCSF+NPY vs. P32/98+NPY ("*"=p<0.05).

Minor effects of P32/98 on feeding. FIG. 8 and FIG. 9 demonstrate that at 1 h NPY produced an "u-shaped" dose-dependent feeding effect (FIG. 8). P32/98 produced a mild feeding effect that only at 0.05 nmol dose reach significance (FIG. 8). Combined treatment of P32/98 followed by NPY differed not from NPY alone (except at highest non-physiological dosages), suggesting that the feeding effect of NPY is not mediated through a mechanisms that is affected by P32/98. Most data in the prior art indicate that the dark cycle feeding effect of NPY is primarily Y5 receptor mediated. Over-night food-intake was not affected by any treatment, except at extremely high dosages (FIG. 9). Thus, central application of the selective DPIV inhibitor P32/98 does not affect major feeding regulatory systems (i.e. the NPY Y5 receptor).

Example 4

In the previous examples we have demonstrated that anxiety and stress-responsiveness were reduced in a genetic model of DPIV deficiency. We further have shown that pharmacological inhibition of CNS DPIV systems results in dose-dependent anxiolytic-like effects in the plus maze, open field and social interaction paradigms of experimental anxiety in rodents. We have shown also, that the magnitude of anxiolysis by P32/98 is similar to that produced by NPY and found that combined application of P32/98 and NPY has additive anxiolytic-like effects in SI test of anxiety, suggesting a potentiation of a NPY Y1 receptor mediated effect. In the present example we report on the mechanism for the potentiation of NPY mediated anxiolytic-like effects at moderate dosages (P32/98, 50 nmol; NPY, 0.8 nmol) as shown in FIG. 7 of Example 3. We confirm that pre-treatment using the NPY Y1 receptor antagonist BIBP3226 can block the P32/98-induced potentiation of the NPY mediated anxiolytic-like effect on SI behavior and furthermore show that 1 h feeding effects are only partly affected by blockade of the Y1R.

Animals. Male WistarF/Han (WF) rats (Central Animal Laboratory, Hannover Medical School, Hannover, Germany, weighing 330±31 g±SD, were housed in a sound-proof, temperature controlled (24.0±0.5° C.) room under specific pathogen free conditions with a 12/12 h dark/light cycle (lights on at 07.00 with illumination level of 80 Lux). Food (Altromin lab chow pellets) and tap water were available ad libitum. Under ketamine/xylasine (100/5 mg/kg, i.p.) anesthesia, the rats were fixed in a Kopf stereotaxic frame and implanted with cannulae (Plastic One, Inc., Roanoke, Va., USA) above the lateral ventricle. All research and animal care procedures were approved by the Lower Saxony district government (Hannover, Germany) and followed principles described in the European Community's Council Directive of 24 Nov. 1986 (86/609/EEC).

Surgery and i.c.v. application. For surgery, rats were anesthetized and prepared with i.c.v. cannulae (coordinates: A: −0.7 mm caudal, L: 1.4 mm lateral to bregma; and V3.2 mm ventral to the skull surface; tooth bar +3.0 above ear bars) using standard stereotaxic procedures as described in detail elsewhere (von Hörsten et al., 1998a, b, c). After a 7-day recovery period, successful ventricle cannulation was confirmed by an angiotensin drinking response (von Hörsten et al., 1998a). Rats showing a positive drinking response (n=56) were then habituated to experimental handling by daily sham injections for seven days.

Animals were randomly divided into eight experimental groups (n=6–8/group), which completed one SI test of anxiety: (1) aCSF+aCSF+aCSF; (2) BIBP+aCSF+aCSF; (3) aCSF+P32/98+aCSF; (4) BIBP+P32/98+aCSF; (5) aCSF+aCSF+NPY; (6) BIBP+aCSF+NPY; (7) aCSF+P32/89+NPY; (8) BIBP+P32/98+NPY. Animals in each group were treated in an identical way in each phase, receiving i.c.v. injections −60 mins and −55 min before behavioral testing. Experiments spanned two nights with groups counterbalances on both dark cycles. The injection cannula was attached to a Hamilton microsyringe with approximately 30 cm of polyethylene tubing and all compounds were infused in a total volume of 5.0 μl at a rate of 5.0 μl/min using a TSE multichannel infusion pump (Bad Homburg, Germany). The time spent in active social interaction (SI-time), 1 h, and 12 h food-intake were measured.

Peptides and Antagonist. Rat neuropeptide $Y_{1-36}$ was obtained from Polypeptide Laboratories (Wolfenbüttel, Germany). The NPY Y1 receptor antagonist BIBP3226 was purchased from American Peptide Company, Sunnyvale, Calif., USA (Cat#: 60-1-22B). All drugs were dissolved in sterile water and final dilutions were made with aCSF.

Social interaction (SI) test. The SI test was carried out as first described by File (1980) and has initially been validated in the laboratory (Kask, Nguyen, Pabst, von Hörsten, submitted). Two rats, matched for treatment, were removed from home cages and exposed to the testing environment. The arena was a squared open field (50×50×50 cm) made of aluminum, placed inside a sound isolation box (Coulboum Instruments, Lehigh Valley, Pa.). For details of the apparatus see our previous study (von Hörsten et al., 1998c). The open field was lit by a red photo light bulb (Philips PF712E; 1.3 Lux). Rats were unfamiliar with the apparatus. Behavior was monitored using a video camera placed above the field inside the testing/isolation box. The SI behavior of both rats was recorded on-line from a monitor placed outside on top of the box. The following parameters were scored by an observer (HPN) unaware of the substrain of rats: duration of time spent in sniffing, following, crawling under and over other rats, but not passive body contact (resting, sleeping). An increase of the SI time is considered an anxiolytic-like response.

Statistical analysis. Data obtained from the measures SI time and 1 h food intake were analyzed by one-way (factor: "treatment") ANOVA. In addition, three factorial (factors: "Antagonist", "Inhibitor", "NPY") ANOVA was performed to confirm general conclusions (data not shown). Asterisks indicate significant post hoc effects vs. aCSF+aCSF+aCSF (Control) while "#" signs indicate a significant difference of Y1R antagonist treatment vs. the corresponding treatment without antagonist obtained by Fisher's PLSD. The level of significance in post hoc comparisons is indicated by asterisks with "*"=$p<0.05$; ""=$p<0.01$; "*"=$p<0.001$) and by "#" symbols with "#"=$p<0.05$; "##"=$p<0.01$; "###"=$p<0.001$). All data are presented as means±S.E.M.

Figure 10:
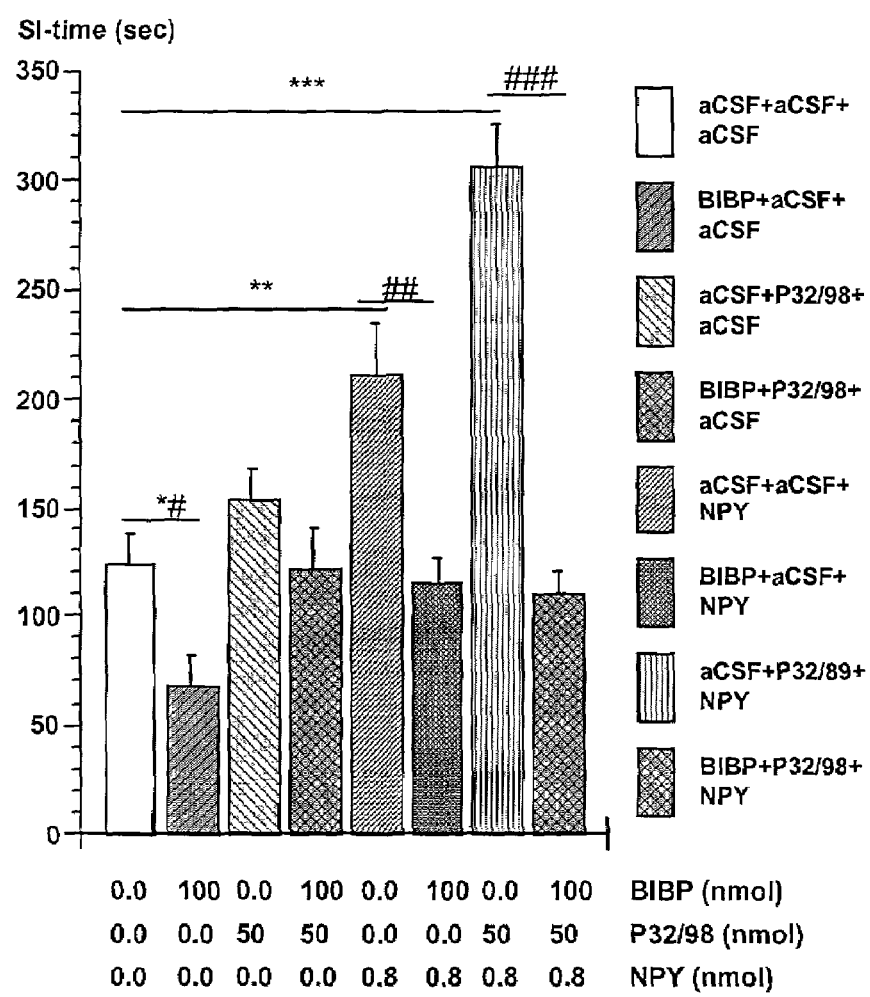
FIG. 10 shows the effect of combined i.c.v. treatment using the Y1R antagonist BIBP3226, P32/98 and NPY in combinations (BIBP3226: 100 nmol; P32/98: 50 nmol; NPY: 0.8 nmol). The time spent in active social interaction (SI-time) in the social interaction test of anxiety was measured. An increase of the SI-time is indicative for an anxiolytic like effect. After habituation to the testing procedure animals were randomly assigned to i.c.v. treatment protocols and same treatment interaction partners. Tests spanned two consecutive with a total of 6–8 animals per treatment condition. Analysis of variance revealed a significant effect of "treatment" with F(7, 44): 33.6, p<0.0001 spanning the following groups: (1) aCSF+aCSF+aCSF; (2) BIBP+aCSF+aCSF; (3) aCSF+P32/98+aCSF; (4) BIBP+P32/98+aCSF; (5) aCSF+aCSF+NPY; (6) BIBP+aCSF+NPY; (7) aCSF+P32/89+NPY; (8) BIBP+P32/98+NPY. The level of significance in post hoc comparisons vs. controls (aCSF+aCSF+aCSF) is indicated by asterisks with "*"=p<0.05; ""=p<0.01; "*"=p<0.001) and vs. corressponding antagonistic treatment (BIBP+n.n.) by "#" symbols with "#"=p<0.05; "##"=p<0.01; "###"=p<0.001). All data are presented as means ±S.E.M.
Figure 11:
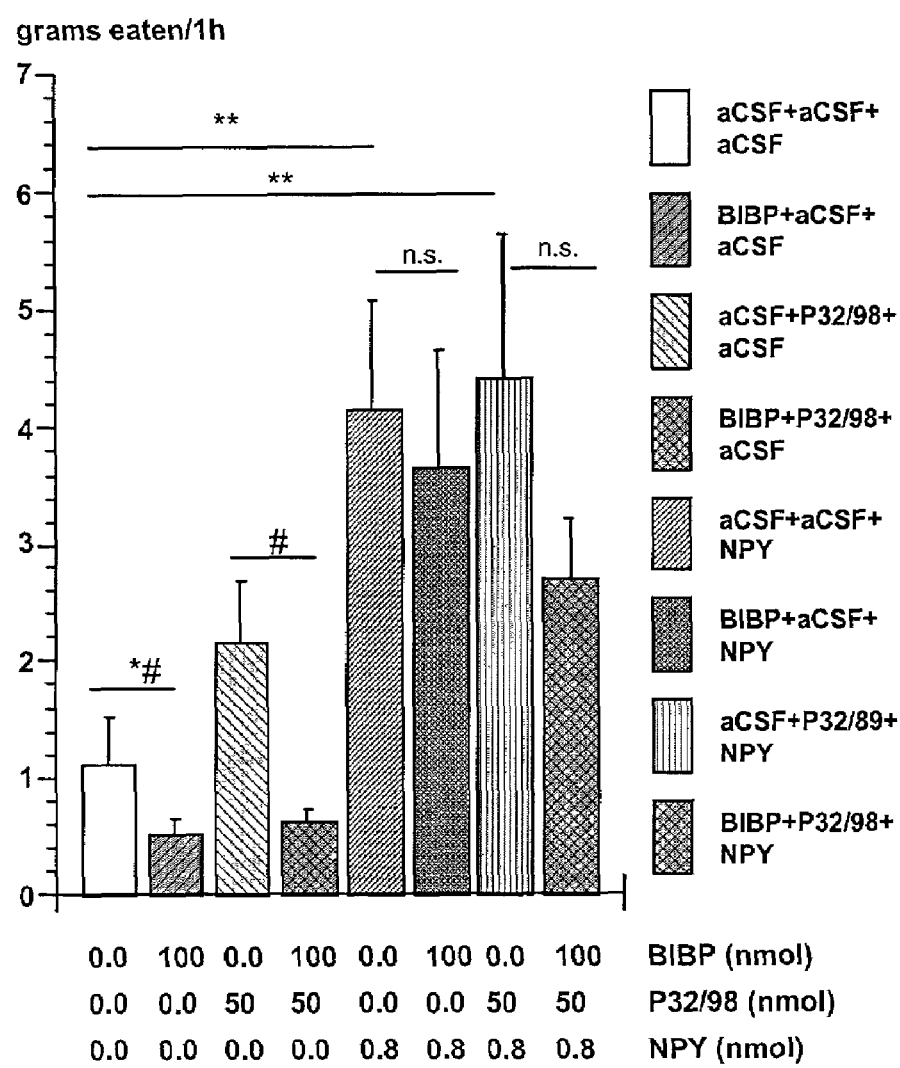
FIG. 11 shows the effect of combined i.c.v. treatment on 1 h food-intake using the Y1R antagonist BIBP3226, P32/98 and NPY in combinations (BIBP3226: 100 nmol; P32/98: 50 nmol; NPY: 0.8 nmol). After habituation to the testing procedure animals were randomly assigned to i.c.v. treatment protocols and same treatment interaction partners. Tests spanned two consecutive with a total of 6–8 animals per treatment condition. Analysis of variance revealed a significant effect of "treatment" with F(7, 44): 5.4, p<0.0002 spanning the following groups: (1) aCSF+aCSF+aCSF; (2) BIBP+aCSF+aCSF; (3) aCSF+P32/98+aCSF; (4) BIBP+P32/98+aCSF; (5) aCSF+aCSF+NPY; (6) BIBP+aCSF+NPY; (7) aCSF+P32/89+NPY; (8) BIBP+P32/98+NPY. The level of significance in post hoc comparisons vs. controls (aCSF+aCSF+aCSF) is indicated by asterisks with "*"=p<0.05; ""=p<0.01; "*"=p<0.001) and vs. corresponding antagonistic treatment (BIBP+n.n.) by "#" symbols with "#"=p<0.05; "##"=p<0.01; "###"=p<0.001). All data are presented as means ±S.E.M.

NPY Y1 receptor mediated potentiation of NPY-induced anxiolysis in the SI test by P32/98 pre-treatment. Combined central administration of P32/98 at a dose of 50 nmol and NPY at a dose of 0.8 nmol dramatically potentiated the anxiolytic-like effect of NPY in the SI test (FIG. 10). This finding replicates at corresponding dosages the observation shown in FIG. 7. At this dose p32/98 treatment alone acts not anxiolytic-like. However, the endogenous social investigatory behavior, the anxiolytic-like effect of NPY and the potentiated anxiolysis induced by combined P32/98+NPY treatment were all antagonized by Y1 receptor blockade. This indicates a tonic regulation of anxiety levels via the NPY Y1 receptor in the CNS and furthermore proofs that the anxiolytic-like effect of NPY as well as the potentiated anxiolysis induced by combined treatment all are primarily Y1 receptor mediated. Spontaneous feeding and NPY-induced feeding are only partly mediated by the Y1R and the non-significant slight increase of feeding induced by P32/98 treatment is blocked by Y1R antagonisms (FIG. 11).

REFERENCES

Aakerlund, L., U. Gether, T. W. Schwartz, and O. Thastrup (1990), Yj receptors for neuropeptide Y are coupled to mobilization of intracellular calcium Agmo, A. and Belzung, C., Interactions between dopamine and GABA in the control of ambulatory activity and neophobia in the mouse, *Pharmacol. Biochem. Behav.*, 59 (1998) 239–247.

Agmo, A. and Belzung, C., The role of subtypes of the opioid receptor in the anxiolytic action of chlordiazepoxide, *Neuropharmacology*, 37 (1998) 223–232.

Agmo, A., Galvan, A., Heredia, A. and Morales, M., Naloxone blocks the antianxiety but not the motor effects of benzodiazepines and pentobarbital: experimental studies and literature review, *Psychopharmacology Berl.*, 120 (1995) 186–194.

Arvat, E., Maccagno, B., Ramunni, J., Di-Vito, L., Gianotti, L., Broglio, F., Benso, A., Deghenghi, R., Camanni, F. and Ghigo, E., Effects of dexamethasone and alprazolam, a benzodiazepine, on the stimulatory effect of hexarelin, a synthetic GHRP, on ACTH, cortisol and GH secretion in humans, *Neuroendocrinology*, 67 (1998) 310–316.

Band, L. C., Pert, A., Williams, W., De Costa, B. R., Rice, K. C. and Weber, R. J., Central µ-opioid receptors mediate suppression of natural killer activity in vivo, *Prog. Neuro. Endocrinol. Immunol.*, 5 (1992) 95–101.

Baram, T. Z., Yi, S., Avishai, E. S. and Schultz, L., Development neurobiology of the stress response: multilevel regulation of corticotropin-releasing hormone function, *Ann. N.Y. Acad. Sci.*, 814 (1997) 252–265.

Baraniuk, J. N., Castellino, S., Lundgren, J. D., Goff, J., Mullol, J., Merida, M., Shelhamer, J, H. and Kaliner, M. A. (1990), Neuropeptide Y (NPY) in human nasal mucosa. *J. Respir. Cell Mol. Biol.* 3, 165–173;

Bard, J. A., Walker, M. W., Branchek, T. A. and Weinshank, R. L. (1995), J. Biol. Chem., 270, 26762–26765. Cloning and functional expression of Y4 subtype receptor for pancreatic polypeptide, neuropeptide Y, and peptide YY.

Bchini-Hooft, v. H.-O., Rohner, J. F. and Jeanrenaud, B., Hypothalamic neuropeptide Y messenger ribonucleic acid levels in pre-obese and genetically obese (fa/fa) rats; potential regulation thereof by corticotropin-releasing factor, *J. Neuroendocrinol.*, 5 (1993) 381–386.

Behan, D. P., De-Souza, E. B., Lowry, P. J., Potter, E., Sawchenko, P. and Vale, W. W., Corticotropin releasing factor (CRF) binding protein: a novel regulator of CRF and related peptides, *Front. Neuroendocrinol.*, 16 (1995) 362–382.

Berkenbosch, F., van-Oers, J., del-Rey, A., Tilders, F. and Besedovsky, H., Corticotropin-releasing factor-producing neurons in the rat activated by interleukin-1, *Science*, 238 (1987) 524–526.

Bertolucci, M., Perego, C. and De Simoni, M. G., Central opiate modulation of peripheral IL-6 in rats, *NeuroReport*, 7 (1996) 1181–1184.

Bertolucci, M., Perego, C. and de Simoni, M. G., Interleukin-6 is differently modulated by central opioid receptor subtypes, *Am. J. Physiol.*, 273 (1997) R956–R959.

Bileviciute, I., Stenfors, C., Theodorsson, E., Beckman, M. and Lundeberg, T., Significant changes in neuropeptide concentrations in the brain of normotensive (WKY) and spontaneously hypertensive (SHR) rats following knee joint monoarthritis, *Brain Res.*, 704 (1995) 71–78.

Britton, D. R., Koob, G. F., Rivier, J. and Vale, W., Intraventricular corticotropin-releasing factor enhances behavioral effects of novelty, *Life Sci.*, 31 (1982) 363–367.

Britton, K. T., Lee, G. and Koob, G. F., Corticotropin releasing factor and amphetamine exaggerate partial agonist properties of benzodiazepine antagonist Ro 15–1788 in the conflict test, *Psychopharmacology Berl.*, 94 (1988) 306–311.

Brown, M. R., Fisher, L. A., Spiess, J., Rivier, J., Rivier, C. and Vale, W., Comparison of the biologic actions of corticotropin-releasing factor and sauvagine, *Regul. Pept.*, 4 (1982) 107–114.

Cabrele, C., (2000), Molecular characterization of the ligand-receptor interaction of the neuropeptide Y family, J. Pept. Sci. 3, 97–122.

Calenco, C. G., Dauge, V., Gacel, G., Feger, J. and Roques, B. P., Opioid delta agonists and endogenous enkephalins induce different emotional reactivity than mu agonists after injection in the rat ventral tegmental area, *Psychopharmacology Berl.*, 103 (1991) 493–502.

Carr, D. J., Rogers, T. J. and Weber, R. J., The relevance of opioids and opioid receptors on immunocompetence and immune homeostasis, *Proc. Soc. Exp. Biol. Med.*, 213 (1996) 248–257.

Chen, C., Dagnino, R., De-Souza, E. B., Grigoriadis, D. E., Huang, C. Q., Kim, K. I., Liu, Z., Moran, T., Webb, T. R., Whitten, J. P., Xie, Y. F. and McCarthy, J. R., Design and synthesis of a series of non-peptide high-affinity human corticotropin-releasing factor1 receptor antagonists, *J. Med. Chem.*, 39 (1996) 4358–4360.

Chronwall, B. M., Anatomy and physiology of the neuroendocrine arcuate nucleus, *Peptides*, 6 Suppl 2 (1985) 1–11.

Clark, J. T., Kalra, P. S., Crowley, W. R. and Kalra, S. P., Neuropeptide Y and human pancreatic polypeptide stimulate feeding behavior in rats, *Endocrinology*, 115 (1984) 427429.

Colmers, W. and Wahlestedt, C. (1993) The biology of neuropeptide Y and related peptides. Humana Press, Totowa, N.J.

Conte, D. B., Rey, M., Boudouresque, F., Giraud, P., Castanas, E., Millet, Y., Codaccioni, J. L. and Oliver, C., Effect of 41-CRF antiserum on the secretion of ACTH, B-endorphin and alpha-MSH in the rat, *Peptides*, 4 (1983) 301–304.

Daniels, A. J., Matthews, J. E., Slepetis, R. J., Jansen, M., Viveros, O. H., Tadepalli, A., Harrington, W., Heyer, D., Landavazo, A., Leban, J. J. and et, a., High-affinity neuropeptide Y receptor antagonists, *Proc. Natl. Acad. Sci. U.S.A.*, 92 (1995) 9067–9071.

Devine, D. P., Taylor, L., Reinscheid, R. K., Monsma-FJ, J., Civelli, O. and Akil, H., Rats rapidly develop tolerance to the locomotor-inhibiting effects of the novel neuropeptide orphanin FQ, *Neurochem. Res.*, 21 (1996) 1387–1396.

Dieterich, K. D., Lehnert, H. and De-Souza, E. B., Corticotropin-releasing factor receptors: an overview, *Exp. Clin. Endocrinol. Diabetes*, 105 (1997) 65–82.

Doods, H. N., Wieland, H. A., Engel, W., Eberlein, W., Willim, K. D., Entzeroth, M., Wienen, W. and Rudolf, K., BIBP 3226, the first selective neuropeptide Y1 receptor antagonist: a review of its pharmacological properties, *Regul. Pept.*, 65 (1996) 71–77.

Dumont, Y., Fournier, A., St, P. S. and Quirion, R., Autoradiographic distribution of [125I]Leu31, Pro34]PYY and [125I]PYY3–36 binding sites in the rat brain evaluated with two newly developed Y1 and Y2 receptor radioligands, *Synapse*, 22 (1996) 139–158.

Dunn, A. J. and Berridge, C. W., Physiological and behavioral responses to corticotropin-releasing factor administration: is CRF a mediator of anxiety or stress responses?, *Brain Res. Brain Res. Rev.*, 15 (1990) 71–100.

Dunn, A. J., Berridge, C. W., Lai, Y. I. and Yachabach, T. L., CRF-induced excessive grooming behavior in rats and mice, *Peptides*, 8 (1987) 841–844.

Egawa, M., Yoshimatsu, H. and Bray, G. A., Effect of corticotropin releasing hormone and neuropeptide Y on electrophysiological activity of sympathetic nerves to interscapular brown adipose tissue, *Neuroscience*, 34 (1990) 771–775.

Egawa, M., Yoshimatsu, H. and Bray, G. A., Neuropeptide Y suppresses sympathetic activity to interscapular brown adipose tissue in rats, *Am. J. Physiol.*, 260 (1991) R328–R334

Eghbal, A. M., Hatalski, C. G., Avishai, E. S. and Baram, T. Z., Corticotropin releasing factor receptor type II (CRF2) messenger ribonucleic acid levels in the hypothalamic ventromedial nucleus of the infant rat are reduced by maternal deprivation, *Endocrinology*, 138 (1997) 5048–5051.

Ehlers, C. L., Henriksen, S. J., Wang, M., Rivier, J., Vale, W. and Bloom, F. E., Corticotropin releasing factor produces increases in brain excitability and convulsive seizures in rats, *Brain Res.*, 278 (1983) 332–336.

Ekman, R., Servenius, B., Castro, M. G., Lowry, P. J., Cederlund, A. S., Bergman, O. and Sjogren, H. O., Biosynthesis of corticotropin-releasing hormone in human T-lymphocytes, *J. Neuroimmunol.*, 44 (1993) 7–13.

Erickson, J. C., Clegg, K. E. and Palmiter, R. D., Sensitivity to leptin and susceptibility to seizures of mice lacking neuropeptide Y [see comments], *Nature*, 381 (1996) 415–421.

Erickson, J. C., Hollopeter, G. and Palmiter, R. D., Attenuation of the obesity syndrome of ob/ob mice by the loss of neuropeptide Y, *Science*, 274 (1996) 1704–1707.

File, S. E., The contribution of behavioural studies to the neuropharmacology of anxiety, *Neuropharmacology*, 26 (1987) 877–886.

Florin, S., Suaudeau, C., Meunier, J. C. and Costentin, J., Nociceptin stimulates locomotion and exploratory behaviour in mice, *Eur. J. Pharmacol.*, 317 (1996) 9–13.

Fuhlendorff, J., U. Gether, L. Aakerlund, N. Langeland-Johansen, H. Togerson, S. GF. Melberg, U. B. Olsen, O. Thastrup, and T. W. Schwartz 31 34 (1990), [LeU, Pro I Neuropeptide Y: A specific Yj receptor agonist, *Proc. Natl. Acad. Sci.* 87, 182–186.

Gaveriaux, R. C., Matthes, H. W., Peluso, J. and Kieffer, B. L., Abolition of morphine-immunosuppression in mice lacking the mu-opioid receptor gene, *Proc. Natl. Acad. Sci. U.S.A.*, 95 (1998) 6326–6330.

Gear, R. W., Miaskowski, C., Heller, P. H., Paul, S. M., Gordon, N. C. and Levine, J. D., Benzodiazepine mediated antagonism of opioid analgesia, *Pain*, 71 (1997) 25–29.

Gehlert, D. R., Multiple receptors for the pancreatic polypeptide (PP-fold) family: physiological implications, *Proc. Soc. Exp. Biol. Med.*, 218 (1998) 7–22.

Gerald, C., Walker, M, W., Criscione, L., Gustafson, E. L., Batzi-Hartmann, C., Smith, K. E, Vaysse, P., Durkin, M. M., Laz. T. M., Linemeyer, D. L., Schaffhauser, A. O., Whitebread, S., Hofbauer, K. G., Taber, R. I., Branchek, T, A. and Weinshank, R. L. (1996). A receptor subtype involved in neuropeptide-Y-induced food intake. *Nature*, 382, 168–171.

Gerald, C., Walker, M. W., Vaysse, P. J.-J, He, C., Branchek, T. A. and Weinshank, R. L. (1995) *J. Biol. Chem.*, 270, 26758–26761. Expression cloning and pharmacological characterisation of a human hippocampal neuropeptide Y/peptide YY Y2 receptor subtype.

Gosnell, B. A., Levine, A. S. and Morley, J. E., The stimulation of food intake by selective agonists of mu, kappa and delta opioid receptors, *Life Sci.*, 38 (1986) 1081–1088.

Grosskreutz, C. L. and Brody, M. J., Regional hemodynamic responses to central administration of corticotropin-releasing factor (CRF), *Brain Res.*, 442 (1988) 363–367.

Grouzmann, E., Buclin, T., Martire, M., Cannizzaro, C., Dorner, B., Razaname, A. and Mutter, M., Characterization of a selective antagonist of neuropeptide Y at the Y2 receptor. Synthesis and pharmacological evaluation of a Y2 antagonist, *J. Biol. Chem.*, 272 (1997) 7699–7706.

Grundemar, L., Grundstrom, N., joahansson, I. G. M., Andersson, R. G. G. and Hakanson, R. (1990) Suppression by neuropeptide Y of capsaicin-sensitive sensory nerve-mediated contraction in guinea-pig airways. Br. J. Pharmacol., 99, 473–476.

Grundemar, L., Wahlestedt, C. and Wang, Z. Y. (1993) Neuropeptide Y suppresses the neurogenic inflammatory response in the rabbit eye; mode of action. Regul. Pept., 43, 57–64.

Grunditz, T., Uddman, R. and Sundler, F. (1994) Origin and peptide content of nerve fibers in the nasal mucosa of rats. Anat. Embryol. 189, 327–337.

Gue, M., Junien, J. L., Reeve-J R, J., Rivier, J., Grandt, D. and Tache, Y., Reversal by NPY, PYY and 3–36 molecular forms of NPY and PYY of intracisternal CRF-induced inhibition of gastric acid secretion in rats, *Br. J. Pharmacol.*, 118 (1996) 237–242.

Heilig, M. and Murison, R., Intracerebroventricular neuropeptide Y suppresses open field and home cage activity in the rat, *Regul. Pept.*, 19 (1987) 221–231.

Heilig, M., B. Söderpalm, J. A. Engel and E. Widerlöv, (1989), Centrally administered neuropeptide Y (NPY) produces anxiolytic-like effects in animal anxiety models, Psychopharmacology, 98, 524–529.

Heilig, M., McLeod, S., Brot, M., Heinrichs, S. C., Menzaghi, F., Koob, G. F. and Britton, K. T., Anxiolytic-like action of neuropeptide Y: mediation by Y1 receptors in amygdala, and dissociation from food intake effects, *Neuropsychopharmacology.*, 8 (1993) 357–363.

Heilig, M., Soderpalm, B., Engel, J. A. and Widerlov, E., Centrally administered neuropeptide Y (NPY) produces anxiolytic-like effects in animal anxiety models, *Psychopharmacology Berl.*, 98 (1989) 524–529.

Heinrichs, S. C., Lapsansky, J., Behan, D. P., Chan, R. K., Sawchenko, P. E., Lorang, M., Ling, N., Vale, W. W. and De-Souza, E. B., Corticotropin-releasing factor-binding protein ligand inhibitor blunts excessive weight gain in genetically obese Zucker rats and rats during nicotine withdrawal, *Proc. Natl. Acad. Sci. U.S.A.*, 93 (1996) 15475–15480.

Heinrichs, S. C., Menzaghi, F., Pich, E. M., Hauger, R. L. and Koob, G. F., Corticotropin-releasing factor in the paraventricular nucleus modulates feeding induced by neuropeptide Y, *Brain Res.*, 611 (1993) 18–24.

Heinrichs, S. C., Pich, E. M., Miczek, K. A., Britton, K. T. and Koob, G. F., Corticotropin-releasing factor antagonist reduces emotionality in socially defeated rats via direct neurotropic action, *Brain Res.*, 581 (1992) 190–197.

Herz, A., Opioid reward mechanisms: a key role in drug abuse?, *Can. J. Physiol. Pharmacol.*, 76 (1998) 252–258.

Herzog, H., Y. J. Hort, H. J. Ball, G. Hayes, J. Shine, and L. A. Selbie (1992), Cloned human neuropeptide Y receptor couples to two different second messenger systems, Proc. Natl. Acad. Sci. U.S.A. 89, 5794–5798.

Hoehe, M. and Duka, T., Opiates increase plasma catecholamines in humans, *Psychoneuroendocrinology.,* 18 (1993) 141–148.

Hoffman, K. E., Maslonek, K. A., Dykstra, L. A. and Lysle, D. T., Effects of central administration of morphine on immune status in Lewis and Wistar rats. In B. M. Sharp, T. K. Eisenstein, J. J. Madden and H. Friedman (Eds.) *The brain immune axis and substance abuse,* Plenum Press, New York, 1995, pp. 155–159.

Hörsten, S. v., Dimitrijevic M., Markovic B. M. and Jankovic B. D., Effect of early experience on behavior and immune response in the rat, *Physiol Behav,* 54 (1993) 931–40.

Hörsten, S. v., Ballof, J., Helfritz, F., Nave, H., Meyer, D., Schmidt, R. E., Stalp, M., Klemm, A., Tschernig, T. and Pabst, R., Modulation of innate immune functions by intracerebroventricularly applied Neuropeptide Y: Dose and time dependent effects, *Life Sci.,* 63 (1998a) 909–922.

Hörsten, S. v., Exton, N. G., Exton, M. S., Helfritz, F., Nave, H., Ballof, J., Stalp, M. and Pabst, R., Brain NPY $Y_1$ receptors rapidly mediate the behavioral response to novelty and a compartment-specific modulation of granulocyte function in blood and spleen, *Brain Res.,* 806 (1998c) 282–286.

Hörsten, S. v., Nave, H., Ballof, J., Helfritz, F., Meyer, D., Schmidt, R. E., Stalp, M., Exton, N. G., Exton, M. S., Straub, R. H., Radulovic, J. and Pabst, R., Centrally applied NPY mimics immunoactivation induced by nonanalgesic doses of Met-Enkephalin, *Neuroreport.,* 9 (1998b) 3881–3885.

Hörsten, S. v., Exton M. S., Voge J., Schult M., Nagel E., Schmidt R. E., Westermann J. and Schedlowski M., Cyclosporine A affects open field behavior in DA rats, *Pharmacol Biochem Behav,* 60 (1998d) 71–6.

Horvath, T. L., Naftolin, F., Kalra, S. P. and Leranth, C., Neuropeptide-Y innervation of beta-endorphin-containing cells in the rat mediobasal hypothalamus: a light and electron microscopic double immunostaining analysis [published erratum appears in Endocrinology 1996 February;137(2):532*]*, *Endocrinology,* 131 (1992) 2461–2467.

Irwin, M., Hauger, R. L. and Britton, K., Benzodiazepines antagonize central corticotropin releasing hormone-induced suppression of natural killer cell activity, *Brain Res.,* 631 (1993) 114–118.

Irwin, M., Stress-induced immune suppression: role of brain corticotropin releasing hormone and autonomic nervous system mechanisms, *Adv. Neuroimmunol.,* 4 (1994) 29–47.

Jankovic, B. D. and Radulovic, J., Enkephalins, brain and immunity: modulation of immune responses by methionine-enkephalin injected into the cerebral cavity, *Int. J. Neurosci.,* 67 (1992) 241–270.

Jenck, F., Moreau, J. L., Martin, J. R., Kilpatrick, G. J., Reinscheid, R. K., Monsma-F J, J., Nothacker, H. P. and Civelli, O., Orphanin FQ acts as an anxiolytic to attenuate behavioral responses to stress, *Proc. Natl. Acad. Sci. U.S.A.,* 94 (1997) 14854–14858.

Judd, S. J., Wong, J., Saloniklis, S., Maiden, M., Yeap, B., Filmer, S. and Michailov, L., The effect of alprazolam on serum cortisol and luteinizing hormone pulsatility in normal women and in women with stress-related anovulation, *J. Clin. Endocrinol. Metab.,* 80 (1995) 818–823.

Kalra, P. S., Norlin, M. and Kalra, S. P., Neuropeptide Y stimulates beta-endorphin release in the basal hypothalamus: role of gonadal steroids, *Brain Res.,* 705 (1995) 353–356.

Karalis, K., Muglia, L. J., Bae, D., Hilderbrand, H. and Majzoub, J. A., CRH and the immune system, *J. Neuroimmunol.,* 72 (1997) 131–136.

Kask, A., L. Rägo and J. Harro, (1998), NPY Y1 receptors in the dorsal periaqueductal gray matter regulate anxiety in the social interaction test, Neuroreport, 9, 2713–2716.

Kask, A., Rago, L. and Harro, J., Anxiolytic-like effect of neuropeptide Y (NPY) and NPY13–36 microinjected into vicinity of locus coeruleus in rats, *Brain Res.,* 788 (1998) 345–348.

Kiritsy, R. J., Appel, N. M., Bobbitt, F. G. and Van-Loon, G. R., Effects of mu-opioid receptor stimulation in the hypothalamic paraventricular nucleus on basal and stress-induced catecholamine secretion and cardiovascular responses, *J. Pharmacol. Exp. Ther.,* 239 (1986) 814–822.

Kiritsy, R. J., Marson, L. and Van-Loon, G. R., Sympathoadrenal, cardiovascular and blood gas responses to highly selective mu and delta opioid peptides, *J. Pharmacol. Exp. Ther.,* 251 (1989) 1096–1103.

Konig, M., Zimmer, A. M., Steiner, H., Holmes, P. V., Crawley, J. N., Brownstein, M. J. and Zimmer, A., Pain responses, anxiety and aggression in mice deficient in pre-proenkephalin, *Nature,* 383 (1996) 535–538.

Koob, G. F. and Bloom, F. E., Corticotropin-releasing factor and behavior, *Fed. Proc.,* 44 (1985) 259–263.

Korbonits, M., Trainer, P. J., Edwards, R., Besser, G. M. and Grossman, A. B., Benzodiazepines attenuate the pituitary-adrenal responses to corticotrophin-releasing hormone in healthy volunteers, but not in patients with Cushing's syndrome, *Clin. Endocrinol. Oxf.,* 43 (1995) 29–35.

Kotz, C. M., Grace, M. K., Billington, C. J. and Levine, A. S., The effect of norbinaltorphimine, beta-funaltrexamine and naltrindole on NPY-induced feeding, *Brain Res.,* 631 (1993) 325–328.

Kravitz, H. M., Fawcett, J. and Newman, A. J., Alprazolam and depression: a review of risks and benefits, *J. Clin. Psychiatry,* 54 Suppl (1993) 78–84.

Kunovac, J. L. and S. M. Stahl, (1995), Future directions in anxiolytic pharmacotherapy, Psychiatr. Clin. North Am., 4, 895–909

Lacroix, J. S., Ulman, L. G. and Potter, E. K. (1994) Modulation by neuropeptide Y of parasympathetic nerve-evoked nasal vasodilitation via Y2 prejunctional receptor. Br. J. Pharmacol., 113, 479–484.

Lambert, P. D., Wilding, J. P., al-Dokhayel, A. A., Gilbey, S. G. and Bloom, S. R., The effect of central blockade of kappa-opioid receptors on neuropeptide Y-induced feeding in the rat, *Brain Res.,* 629 (1993) 146–148.

Leu, S. J. and Singh, V. K., Modulation of natural killer cell-mediated lysis by corticotropin-releasing neurohormone, *J. Neuroimmunol.,* 33 (1991) 253–260.

Levine, A. S. and Billington, C. J., Opioids. Are they regulators of feeding?, *Ann. N. Y. Acad. Sci.,* 575 (1989) 209–219.

Linthorst, A. C., Flachskamm, C., Hopkins, S. J., Hoadley, M. E., Labeur, M. S., Holsboer, F. and Reul, J. M., Long-term intracerebroventricular infusion of corticotropin-releasing hormone alters neuroendocrine, neurochemical, autonomic, behavioral, and cytokine responses to a systemic inflammatory challenge, *J. Neurosci.,* 17 (1997) 4448–4460.

Locke, K. W. and Holtzman, S. G., Behavioral effects of opioid peptides selective for mu or delta receptors. I.

Morphine-like discriminative stimulus effects, *J. Pharmacol. Exp. Ther.*, 238 (1986) 990–996.

Loh, H. H., Liu, H. C., Cavalli, A., Yang, W., Chen, Y. F. and Wei, L. N., mu Opioid receptor knockout in mice: effects on ligand-induced analgesia and morphine lethality, *Brain Res. Mol. Brain Res.*, 54 (1998) 321–326.

Lundberg, J. M., Pharmacology of cotransmission in the autonomic nervous system: Intergrative aspects on amines, neruopeptides, adenosine triphosphaste, amino acids and nitric oxide, Pharmacol. Rev., 48 (1996) 113–178.

Lundberg, J. M., Hensen, A., Larsson, O., Rudehill, A., Saria, A & Fredholm B. B., (1988). Neuropeptide Y receptor in pig spleen; binding characteristics, reduction of cAMP formation and calcium antagonist inhibition of vasoconstriction. Eur. J. Pharmacol. Vol. 45; 21–29

Lysle, D. T., Hoffman, K. E. and Dykstra, L. A., Evidence for the involvement of the caudal region of the periaqueductal gray in a subset of morphine-induced alterations of immune status, *J. Pharmacol. Exp. Ther.*, 277 (1996) 1533–1540.

Makino, S., Takemura, T., Asaba, K., Nishiyama, M., Takao, T. and Hashimoto, K., Differential regulation of type-1 and type-2alpha corticotropin-releasing hormone receptor mRNA in the hypothalamic paraventricular nucleus of the rat, *Brain Res. Mol. Brain Res.*, 47 (1997) 170–176.

Mamiya, T., Noda, Y., Nishi, M., Takeshima, H. and Nabeshima, T., Enhancement of spatial attention in nociceptin/orphanin FQ receptor-knockout mice, *Brain Res.*, 783 (1998) 236–240.

Manabe, T., Noda, Y., Mamiya, T., Katagiri, H., Houtani, T., Nishi, M., Noda, T., Takahashi, T., Sugimoto, T., Nabeshima, T. and Takeshima, H., Facilitation of long-term potentiation and memory in mice lacking nociceptin receptors, *Nature*, 394 (1998) 577–581.

Marsh, D. J., Hollopeter, G., Kafer, K. E. and Palmiter, R. D., Role of the Y5 neuropeptide Y receptor in feeding and obesity [see comments], *Nat. Med.*, 4 (1998) 718–721.

Matthes, H. W., Maldonado, R., Simonin, F., Valverde, O., Slowe, S., Kitchen, I., Befort, K., Dierich, A., Le-Meur, M., Dolle, P., Tzavara, E., Hanoune, J., Roques, B. P. and Kieffer, B. L., Loss of morphine-induced analgesia, reward effect and withdrawal symptoms in mice lacking the mu-opioid-receptor gene [see comments], *Nature*, 383 (1996) 819–823.

May, C. N., Dashwood, M. R., Whitehead, C. J. and Mathias, C. J., Differential cardiovascular and respiratory responses to central administration of selective opioid agonists in conscious rabbits: correlation with receptor distribution, *Br. J. Pharmacol*, 98 (1989) 903–913.

Mellado, M. L., Gibert, R. J., Chover, A. J. and Mico, J. A., Effect on nociception of intracerebroventricular administration of low doses of neuropeptide Y in mice, *Life Sci.*, 58 (1996) 2409–2414.

Mellon, R. D. and Bayer, B. M., Evidence for central opioid receptors in the immunomodulatory effects of morphine: review of potential mechanism(s) of action, *J. Neuroimmunol.*, 83 (1998) 19–28.

Mellon, R. D. and Bayer, B. M., Role of central opioid receptor subtypes in morphine-induced alterations in peripheral lymphocyte activity, *Brain Res.*, 789 (1998) 56–67.

Mentlein, R., P. Dahms, D. Grandt and R. Krüger, (1993), Proteolytic processing of neuropeptide Y and peptide YY by dipeptidyl peptidase IV, Regul. Pept. 49, 133–144.

Menzaghi, F., Heinrichs, S. C., Pich, E. M., Tilders, F. J. and Koob, G. F., Functional impairment of hypothalamic corticotropin-releasing factor neurons with immunotargeted toxins enhances food intake induced by neuropeptide Y, *Brain Res.*, 618 (1993) 76–82.

Menzaghi, F., Howard, R. L., Heinrichs, S. C., Vale, W., Rivier, J. and Koob, G. F., Characterization of a novel and potent corticotropin-releasing factor antagonist in rats, *J. Pharmacol. Exp. Ther.*, 269 (1994) 564–572.

Mercer, M. E. and Holder, M. D., Food cravings, endogenous opioid peptides, and food intake: a review, *Appetite.*, 29 (1997) 325–352.

Meunier, J. C., Mollereau, C., Toll, L., Suaudeau, C., Moisand, C., Alvinerie, P., Butour, J. L., Guillemot, J. C., Ferrara, P., Monsarrat, B. and et, a., Isolation and structure of the endogenous agonist of opioid receptor-like ORL1 receptor [see comments], *Nature*, 377 (1995) 532–535.

Millan, M. J., Kappa-opioid receptors and analgesia, *Trends. Pharmacol. Sci.*, 11 (1990) 70–76.

Minami, M. and Satoh, M., Molecular biology of the opioid receptors: structures, functions and distributions, *Neurosci. Res.*, 23 (1995) 121–145.

Mogil, J. S., Grisel, J. E., Reinscheid, R. K., Civelli, O., Belknap, J. K. and Grandy, D. K., Orphanin FQ is a functional anti-opioid peptide, *Neuroscience*, 75 (1996) 333–337.

Mollereau, C., Parmentier, M., Mailleux, P., Butour, J. L., Moisand, C., Chalon, P., Caput, D., Vassart, G. and Meunier, J. C., ORL1, a novel member of the opioid receptor family. Cloning, functional expression and localization, *FEBS Lett.*, 341 (1994) 33–38.

Motta, V. and Brandao, M. L., Aversive and antiaversive effects of morphine in the dorsal periaqueductal gray of rats submitted to the elevated plus-maze test *Pharmacol. Biochem. Behav.*, 44 (1993) 119–125.

Nishi, M., Houtani, T., Noda, Y., Mamiya, T., Sato, K., Doi, T., Kuno, J., Takeshima, H., Nukada, T., Nabeshima, T., Yamashita, T., Noda, T. and Sugimoto, T., Unrestrained nociceptive response and disregulation of hearing ability in mice lacking the nociceptin/orphaninFQ receptor, *EMBO J.*, 16 (1997) 1858–1864.

Noble, F., Smadja, C., Valverde, O., Maldonado, R., Coric, P., Turcaud, S., Fournie, Z. M. and Roques, B. P., Pain-suppressive effects on various nociceptive stimuli (thermal, chemical, electrical and inflammatory) of the first orally active enkephalin-metabolizing enzyme inhibitor RB 120, *Pain*, 73 (1997) 383–391.

Noda, Y., Mamiya, T., Nabeshima, T., Nishi, M., Higashioka, M. and Takeshima, H., Loss of antinociception induced by naloxone benzoylhydrazone in nociceptin receptor-knockout mice, *J. Biol. Chem.*, 273 (1998) 18047–18051.

Novak, J. E., Gomez-Flores, R., Calderon, S. N., Rice, K. C. and Weber, R. J., Rat natural killer cell, T cell and macrophage functions after intracerebroventricular injection of SNC80, *J. Pharmacol. Exp. Ther.*, 286 (1998) 931–937.

Olson, G. A., Olson, R. D. and Kastin, A. J., Endogenous opiates: 1995, *Peptides*, 17 (1996) 1421–1466.

Ono, N., Lumpkin, M. D., Samson, W. K., McDonald, J. K. and McCann, S. M., Intrahypothalamic action of corticotrophin-releasing factor (CRF) to inhibit growth hormone and LH release in the rat, *Life Sci.*, 35 (1984) 1117–1123.

O'Shea, D., Morgan, D. G., Meeran, K., Edwards, C. M., Turton, M. D., Choi, S. J., Heath, M. M., Gunn, I., Taylor, G. M., Howard, J. K., Bloom, C. I., Small, C. J., Haddo, O., Ma, J. J., Callinan, W., Smith, D. M., Ghatei, M. A.

and Bloom, S. R., Neuropeptide Y induced feeding in the rat is mediated by a novel receptor, *Endocrinology*, 138 (1997) 196–202.

Owens, M. J. and Nemeroff, C. B., Physiology and pharmacology of corticotropin-releasing factor, *Pharmacol. Rev.*, 43 (1991) 425–473.

Pechnick, R. N., Effects of opioids on the hypothalamo-pituitary-adrenal axis, *Annu. Rev. Pharmacol. Toxicol.*, 33 (1993) 353–382.

Pedrazzini, T., Seydoux, J., Kunstner, P., Aubert, J. F., Grouzmann, E., Beermann, F. and Brunner, H. R., Cardiovascular response, feeding behavior and locomotor activity in mice lacking the NPY Y1 receptor [see comments], *Nat. Med.*, 4 (1998) 722–726.

Pfeiffer, A., Brantl, V., Herz, A. and Emrich, H. M., Psychotomimesis mediated by kappa opiate receptors, *Science*, 233 (1986) 774–776.

Pomonis, J. D., Billington, C. J. and Levine, A. S., Orphanin FQ, agonist of orphan opioid receptor ORL1, stimulates feeding in rats, *Neuroreport.*, 8 (1996) 369–371.

Potter, E. K. and M. J, D. McCloskey, (1992), [Leu 3', Leu 34 1 neuropeptide Y, a 45 selective functional agonist at neuropeptide Y receptors in anaesthetised rats, Neurosci. Lett. 134, 183–186, Potter, EX, J. Fuhlendorff and T. W. Schwartz (1991), [Pro34 J neuropeptide Y selectively identifies postjunctional-mediated actions of neuropeptide Y in idvo in rats and dogs, Eur. J. Pharmacol. 193, 15–19.

Potter, EX, Mitchell, L., McCloskey, M. J., Tseng, A., Goodman, A. E., Shine, J. and McCloskey, D. I. (1989) Pre-and postjunctional actions of neuropeptide Y and related peptides. Regul. Pept. 25, 167–177.

Privette, T. H. and Terrian, D. M., Kappa opioid agonists produce anxiolytic-like behavior on the elevated plus-maze, *Psychopharmacology Berl.*, 118 (1995) 444–450.

Radulovic, J. and Jankovic, B. D., Opposing activities of brain opioid receptors in the regulation of humoral and cell-mediated immune responses in the rat, *Brain Res.*, 661 (1994) 189–195.

Radulovic, J., Miljevic, C., Djergovic, D., Vujic, V., Antic, J., von-Hörsten, S. and Jankovic, B. D., Opioid receptor-mediated suppression of humoral immune response in vivo and in vitro: involvement of kappa opioid receptors, *J. Neuroimmunol.*, 57 (1995) 55–62.

Rassnick, S., Heinrichs, S. C., Britton, K. T. and Koob, G. F., Microinjection of a corticotropin-releasing factor antagonist into the central nucleus of the amygdala reverses anxiogenic-like effects of ethanol withdrawal, *Brain Res.*, 605 (1993) 25–32.

Reinscheid, R. K., Nothacker, H. P., Bourson, A., Ardati, A., Henningsen, R. A., Bunzow, J. R., Grandy, D. K., Langen, H., Monsma-F J, J. and Civelli, O., Orphanin F Q: a neuropeptide that activates an opioidlike G protein-coupled receptor, *Science*, 270 (1995) 792–794.

Rioux, F., H. Bachelard, J. C. Martel and S. St.-Piere, (1986), The vasoconstrictor effect of neuropeptide Y and related peptides in the guinea pig isolated heart, Peptides, 7, 27–31.

Risdahl, J. M., Khanna, K. V., Peterson, P. K. and Molitor, T. W., Opiates and infection, *J. Neuroimmunol*, 83 (1998) 4–18.

Rivier, C., Rivier, J., Mormede, P. and Vale, W., Studies of the nature of the interaction between vasopressin and corticotropin-releasing factor on adrenocorticotropin release in the rat, *Endocrinology*, 115 (1984) 882–886.

Rivier, C. L. and Plotsky, P. M., Mediation by corticotropin releasing factor (CRF) of adenohypophysial hormone secretion, *Annu. Rev. Physiol.*, 48 (1986) 475–494.

Rossi, G. C., Leventhal, L. and Pasternak, G. W., Naloxone sensitive orphanin FQ-induced analgesia in mice, *Eur. J. Pharmacol.*, 311 (1996) R7–R8

Sainsbury, A., Rohner, J. F., Cusin, I., Zakrzewska, K. E., Halban, P. A., Gaillard, R. C. and Jeanrenaud, B., Chronic central neuropeptide Y infusion in normal rats: status of the hypothalamo-pituitary-adrenal axis, and vagal mediation of hyperinsulinaemia, *Diabetologia*, 40 (1997) 1269–1277.

Sandin, J., Georgieva, J., Schott, P. A., Ogren, S. O. and Terenius, L., Nociceptin/orphanin FQ microinjected into hippocampus impairs spatial learning in rats, *Eur. J. Neurosci.*, 9 (1997) 194–197.

Saperstein, A., Brand, H., Audhya, T., Nabriski, D., Hutchinson, B., Rosenzweig, S. and Hollander, C. S., Interleukin 1 beta mediates stress-induced immunosuppression via corticotropin-releasing factor, *Endocrinology*, 130 (1992) 152–158.

Satoh, M. and Minami, M., Molecular pharmacology of the opioid receptors, *Pharmacol. Ther.*, 68 (1995) 343–364.

Schwartz, T. W., J. Fuhlendorff, H, Langeland, J. C. T6gerson, S. P. Sheikh, (1989), in Neuropeptide Y–XIV Nobel Symposium, ed: V. Mutt; T. H6kfelt, K. Fuxe and J. M. Lundberg, Raven, N. Y. pp 143.

Shavit, J. (1991) Stress-induced immune modulation in animals: opiates and endogenous opioid peptides. In: R. Ader, D. L. Felten and N. Cohen (Eds.), Psychoneuroimmunology, Vol. Academic Press, San Diego, pp. 789–804.

Shavit, Y., Depaulis, A., Martin, F. C., Terman, G. W., Pechnick, R. N., Zane, C. J., Gale, R. P. and Liebeskind, J. C., Involvement of brain opiate receptors in the immune-suppressive effect of morphine, *Proc. Natl. Acad. Sci. U.S.A.*, 83 (1986) 7114–7117.

Sheikh, S. P., R. HAkanson and T. W. Schwartz, (1989), Yj and Y2 receptors for neuropeptide Y, FEBS Lett. 245, 209–214.

Shippenberg, T. S., Bals, K. R. and Herz, A., Motivational properties of opioids: evidence that an activation of delta-receptors mediates reinforcement processes, *Brain Res.*, 436 (1987) 234–239.

Simonin, F., Valverde, O., Smadja, C., Slowe, S., Kitchen, I., Dierich, A., Le-Meur, M., Roques, B. P., Maldonado, R. and Kieffer, B. L., Disruption of the kappa-opioid receptor gene in mice enhances sensitivity to chemical visceral pain, impairs pharmacological actions of the selective kappa-agonist U-50,488H and attenuates morphine withdrawal, *EMBO J.*, 17 (1998) 886–897.

Smith, C. C., Hauser, E., Renaud, N. K., Leff, A., Aksentijevich, S., Chrousos, G. P., Wilder, R. L., Gold, P. W. and Stemberg, E. M., Increased hypothalamic [3H]flunitrazepam binding in hypothalamic-pituitary-adrenal axis hyporesponsive Lewis rats, *Brain Res.*, 569 (1992) 295–299.

Sora, I., Funada, M. and Uhl, G. R., The mu-opioid receptor is necessary for [D-Pen2, D-Pen5]enkephalin-induced analgesia, *Eur. J. Pharmacol.*, 324 (1997) R1–R2

Stanley, B. G. and Leibowitz, S. F., Neuropeptide Y injected in the paraventricular hypothalamus: a powerful stimulant of feeding behavior, *Proc. Natl. Acad. Sci. U.S.A.*, 82 (1985) 3940–3943.

Stanley, B. G., Lanthier, D., Chin, A. S. and Leibowitz, S. F., Suppression of neuropeptide Y-elicited eating by adrenalectomy or hypophysectomy: reversal with corticosterone, *Brain Res.*, 501 (1989) 32–36.

Stefano, G. B., Salzet, B. and Fricchione, G. L., Enkelytin and opioid peptide association in invertebrates and vertebrates: immune activation and pain, *Immunol. Today,* 19 (1998) 265–268.

Tatemoto, K., Carlquist, M. and Mutt, V., Neuropeptide Y—a novel brain peptide with structural similarities to peptide YY and pancreatic polypeptide, *Nature,* 296 (1982) 659–660.

Tatemoto, K., Neuropeptide Y: complete amino acid sequence of the brain peptide, *Proc. Natl. Acad. Sci. U.S.A.,* 79 (1982) 5485–5489.

Tejedor, R. P., Costela, C. and Gibert, R. J., Neonatal handling reduces emotional reactivity and susceptibility to learned helplessness. Involvement of catecholaminergic systems, *Life Sci.,* 62 (1998) 37–50.

Tian, M., Broxmeyer, H. E., Fan, Y., Lai, Z., Zhang, S., Aronica, S., Cooper, S., Bigsby, R. M., Steinmetz, R., Engle, S. J., Mestek, A., Pollock, J. D., Lehman, M. N., Jansen, H. T., Ying, M., Stambrook, P. J., Tischfield, J. A. and Yu, L., Altered hematopoiesis, behavior, and sexual function in mu opioid receptor-deficient mice, *J. Exp. Med.,* 185 (1997) 1517–1522.

Torpy, D. J., Grice, J. E., Hockings, G. I., Walters, M. M., Crosbie, G. V. and Jackson, R. V., Alprazolam blocks the naloxone-stimulated hypothalamo-pituitary-adrenal axis in man, *J. Clin. Endocrinol. Metab.,* 76 (1993) 388–391.

Tortella, F. C. and DeCoster, M. A., Kappa opioids: therapeutic considerations in epilepsy and CNS injury, *Clin. Neuropharmacol.,* 17 (1994) 403–416.

Tsuda, M., Suzuki, T., Misawa, M. and Nagase, H., Involvement of the opioid system in the anxiolytic effect of diazepam in mice, *Eur. J. Pharmacol.,* 307 (1996) 7–14.

Uehara, Y., Shimizu, H., Ohtani, K., Sato, N. and Mori, M., Hypothalamic corticotropin-releasing hormone is a mediator of the anorexigenic effect of leptin, *Diabetes,* 47 (1998) 890–893.

van-Dijk, G., Bottone, A. E., Strubbe, J. H. and Steffens, A. B., Hormonal and metabolic effects of paraventricular hypothalamic administration of neuropeptide Y during rest and feeding, *Brain Res.,* 660 (1994) 96–103.

Vaughan, J., Donaldson, C., Bittencourt, J., Perrin, M. H., Lewis, K., Sutton, S., Chan, R., Turnbull, A. V., Lovejoy, D., Rivier, C. and et, a., Urocortin, a mammalian neuropeptide related to fish urotensin I and to corticotropin-releasing factor [see comments], *Nature,* 378 (1995) 287–292.

Vezzani, A., Schwarzer, C., Lothman, E. W., Williamson, J. and Sperk, G., Functional changes in somatostatin and neuropeptide Y containing neurons in the rat hippocampus in chronic models of limbic seizures, *Epilepsy Res.,* 26 (1996) 267–279.

Wahlestedt, C. and Reis, D. J., Neuropeptide Y-related peptides and their receptors—are the receptors potential therapeutic drug targets?, *Annu. Rev. Pharmacol. Toxicol.,* 33 (1993) 309–352.

Wahlestedt, C., N. Yanaihara and R. H. Akanson, (1986), Evidence for different pre- and post-junctional receptors for neuropeptide Y and related peptides, *Regul. Pep.* 13, 307–318.

Wahlestedt, C., Pich, E. M., Koob, G. F., Yee, F. and Heilig, M., Modulation of anxiety and neuropeptide Y–Y1 receptors by antisense oligodeoxynucleotides, *Science,* 259 (1993) 528–531.

Wettstein, J. G., Earley, B. and Junien, J. L., Central nervous system pharmacology of neuropeptide Y, *Pharmacol. Ther.,* 65 (1995) 397–414.

Wilder, R. L., Corticotropin releasing hormone and the hypothalamic-pituitary-adrenal axis in the regulation of inflammatory arthritis, *Agents Actions Suppl.,* 41 (1993) 3–9.

Woldbye, D. P., Larsen, P. J., Mikkelsen, J. D., Klemp, K., Madsen, T. M. and Bolwig, T. G. Powerful inhibition of kainic acid seizures by neuropeptide Y via Y5-like receptors [see comments], *Nat. Med.,* 3 (1997) 761–764.

Xu, X. J., Hao, J. X. and Wiesenfeld, H. Z., Nociceptin or antinociceptin: potent spinal antinociceptive effect of orphanin FQ/nociceptin in the rat, *Neuroreport.,* 7 (1996) 2092–2094.

Zadina, J. E., Hackler, L., Ge, L. J. and Kastin, A. J., A potent and selective endogenous agonist for the mu-opiate receptor [see comments], *Nature,* 386 (1997) 499–502.

Zhao, X. J., Hoheisel, G., Schauer, J. and Bornstein, S. R., Corticotropin-releasing hormone-binding protein and its possible role in neuroendocrinological research, *Horm. Metab. Res.,* 29 (1997) 373–378.

Zhu, Y. and Im, W. B., Block of sodium channel current by anticonvulsant U-54494A in mouse neuroblastoma cells, *J. Pharmacol. Exp. Ther.,* 260 (1992) 110–116.

What is claimed is:

1. A method of treating anxiety comprising introducing into the central nervous system a therapeutically effective amount of an inhibitor of dipeptidyl peptidase IV enzyme formulated in combination with neuropeptide Y.

2. The method of claim 1 wherein said introducing of said inhibitor of dipeptidyl peptidase IV enzyme in combination with neuropeptide Y is parenteral.

3. The method of claim 1, wherein said inhibitor of dipeptidyl peptidase IV enzyme is selected from the group con g of N—(N'-substituted glycyl)-2-cyanopyrrolidines, L-threo-isoleucyl thiazolidine, L-threo-isoleucyl pyrrolidine, L-allo-isoleucyl thiazolidine and L-allo-isoleucyl pyrrolidine.

* * * * *

UNITED STATES PATENT AND TRADEMARK OFFICE
CERTIFICATE OF CORRECTION

PATENT NO.        : 7,132,104 B1
APPLICATION NO.   : 10/014291
DATED             : November 7, 2006
INVENTOR(S)       : Stephan von Hoersten et al.

It is certified that error appears in the above-identified patent and that said Letters Patent is hereby corrected as shown below:

(75) INVENTORS:

"Stephan von Horsten"

should be

--Stephan von Hoersten--

IN THE CLAIMS

Column 36; Line 50

"con g"

should be --consisting--

Signed and Sealed this

Ninth Day of January, 2007

JON W. DUDAS
*Director of the United States Patent and Trademark Office*